US010898620B2

(12) United States Patent
Ramzipoor et al.

(10) Patent No.: US 10,898,620 B2
(45) Date of Patent: Jan. 26, 2021

(54) COMPOSITE STENT HAVING MULTI-AXIAL FLEXIBILITY AND METHOD OF MANUFACTURE THEREOF

(71) Applicant: Razmodics LLC, Novato, CA (US)

(72) Inventors: Kamal Ramzipoor, Fremont, CA (US); Richard J. Saunders, Redwood City, CA (US)

(73) Assignee: Razmodics LLC, Novato, CA (US)

( * ) Notice: Subject to any disclaimer, the term of this patent is extended or adjusted under 35 U.S.C. 154(b) by 600 days.

(21) Appl. No.: 15/624,235

(22) Filed: Jun. 15, 2017

(65) Prior Publication Data
US 2017/0281832 A1    Oct. 5, 2017

Related U.S. Application Data

(60) Continuation-in-part of application No. 15/439,002, filed on Feb. 22, 2017, now abandoned, which is a
(Continued)

(51) Int. Cl.
*A61L 31/14*    (2006.01)
*A61L 31/04*    (2006.01)
(Continued)

(52) U.S. Cl.
CPC ............ *A61L 31/148* (2013.01); *A61F 2/07* (2013.01); *A61F 2/82* (2013.01); *A61L 31/04* (2013.01);
(Continued)

(58) Field of Classification Search
CPC . A61F 2/07; A61F 2/82; A61L 31/148; A61L 31/04; A61L 31/06; A61L 31/14; A61L 31/16
See application file for complete search history.

(56) References Cited

U.S. PATENT DOCUMENTS 5,824,049 A * 10/1998 Ragheb .................... A61F 2/82
                                                     623/1.44
5,827,321 A * 10/1998 Roubin .................... A61F 2/91
                                                     623/1.16
(Continued)

OTHER PUBLICATIONS

"Polylactic acid" https://en.wikipedia.org/wiki/Polylactic_acid, description of material characteristics of PLLA retrieved Mar. 4, 2018.
(Continued)

*Primary Examiner* — Jennifer Dieterle
*Assistant Examiner* — Tiffany P Shipmon
(74) *Attorney, Agent, or Firm* — Levine Bagade Han LLP

(57) ABSTRACT

A bioabsorbable composite stent structure, comprising bioabsorbable polymeric ring structures which retain a molecular weight and mechanical strength of a starting substrate and one or more interconnecting struts which extend between and couple adjacent ring structures. The ring structures can have a formed first diameter and being radially compressible to a smaller second diameter and re-expandable to the first diameter. The ring structures can comprise a base polymeric layer. The interconnecting struts can be formed from a polymer blend or co-polymer of poly-L-lactide (PLLA) and an elastomeric polymer. The interconnecting struts each can have a width that is less than a circumference of one of the ring structures. The adjacent ring structures can be axially and rotationally movable relative to one another via the interconnecting struts. The interconnecting struts can also be bioabsorbable.

20 Claims, 17 Drawing Sheets

Related U.S. Application Data continuation of application No. 13/476,853, filed on May 21, 2012, now Pat. No. 10,646,359, which is a division of application No. 12/143,659, filed on Jun. 20, 2008, now Pat. No. 8,206,635, application No. 15/624,235, filed on Jun. 15, 2017, which is a continuation-in-part of application No. 12/541,095, filed on Aug. 13, 2009, now abandoned.

(60) Provisional application No. 61/088,433, filed on Aug. 13, 2008.

(51) Int. Cl.

| | | |
|---|---|---|
| *A61F 2/82* | (2013.01) | |
| *A61F 2/07* | (2013.01) | |
| *B29C 41/14* | (2006.01) | |
| *A61L 31/16* | (2006.01) | |
| *A61L 31/06* | (2006.01) | |
| *B29C 41/00* | (2006.01) | |
| *A61F 2/30* | (2006.01) | |
| *B29C 49/00* | (2006.01) | |
| *A61F 2/24* | (2006.01) | |
| *B29L 31/00* | (2006.01) | |
| *B29K 105/00* | (2006.01) | |

(52) U.S. Cl.
CPC ............... *A61L 31/06* (2013.01); *A61L 31/14* (2013.01); *A61L 31/16* (2013.01); *B29C 41/003* (2013.01); *B29C 41/14* (2013.01); *A61F 2/24* (2013.01); *A61F 2002/30062* (2013.01); *A61F 2002/30535* (2013.01); *A61F 2210/0004* (2013.01); *A61F 2210/0019* (2013.01); *A61F 2240/004* (2013.01); *B29C 49/00* (2013.01); *B29K 2105/0035* (2013.01); *B29K 2995/0056* (2013.01); *B29L 2031/7532* (2013.01)

(56) References Cited

U.S. PATENT DOCUMENTS

| | | |
|---|---|---|
| 5,922,393 A | 7/1999 | Jayaraman |
| 6,214,115 B1 | 4/2001 | Taylor et al. |
| 9,675,478 B2 | 6/2017 | Pacetti et al. |
| 9,908,143 B2 | 3/2018 | Ramzipoor et al. |
| 10,646,359 B2 | 5/2020 | Ramzipoor et al. |
| 2002/0116052 A1 | 8/2002 | Cox et al. |
| 2003/0215564 A1 | 11/2003 | Heller et al. |
| 2005/0182480 A1 | 8/2005 | Doran et al. |
| 2005/0271701 A1* | 12/2005 | Cottone, Jr. .............. A61F 2/86 424/426 |
| 2007/0078513 A1 | 4/2007 | Campbell |
| 2007/0135905 A1 | 6/2007 | Bergermeister et al. |
| 2007/0154512 A1 | 7/2007 | Dave et al. |
| 2007/0179219 A1 | 8/2007 | Huang et al. |
| 2007/0182041 A1 | 8/2007 | Rizk et al. |
| 2007/0253999 A1 | 11/2007 | Huang et al. |

OTHER PUBLICATIONS

Middleton et al., "Synthetic biodegradable polymers as orthopedic devices", Biomaterials 2000, vol. 21, pp. 2335-2346.

* cited by examiner

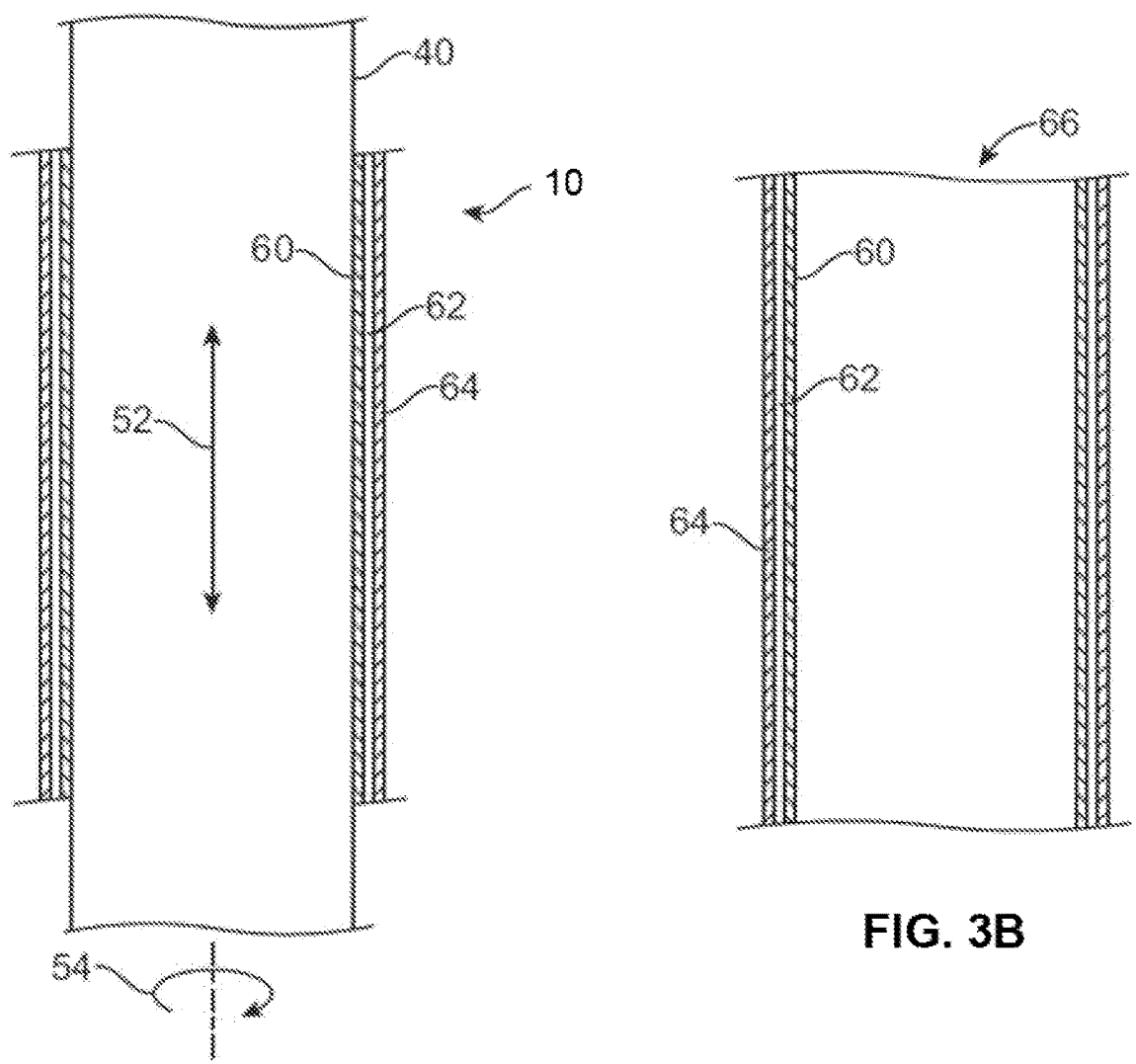
FIG. 3A
FIG. 3B
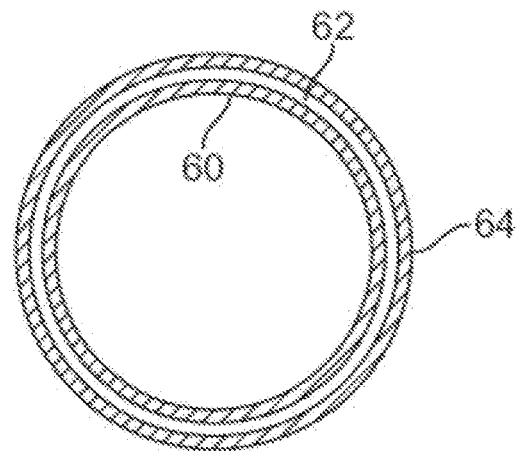
FIG. 3C

COMPOSITE STENT HAVING MULTI-AXIAL FLEXIBILITY AND METHOD OF MANUFACTURE THEREOF

CROSS-REFERENCE TO RELATED APPLICATIONS

This application is a continuation-in-part of U.S. patent application Ser. No. 15/439,002, filed on Feb. 22, 2017, which is a continuation of U.S. patent application Ser. No. 13/476,853, filed on May 21, 2012, which is a divisional of U.S. patent application Ser. No. 12/143,659, filed on Jun. 20, 2008 (now U.S. Pat. No. 8,206,635 issued Jun. 26, 2012) and a continuation-in-part of U.S. patent application Ser. No. 12/541,095, filed on Aug. 13, 2009, which claims the benefit of priority to U.S. Prov. Pat. App. No. 61/088,433, filed on Aug. 13, 2008, all of which are incorporated herein by reference in their entireties.

TECHNICAL FIELD

The present invention relates generally to composite prostheses which are implantable within a patient. More particularly, the present invention relates to implantable prostheses which utilize a composite structure having various geometries suitable for implantation within an artery of a patient, such as the superficial femoral artery (SFA) of the patient.

BACKGROUND

In recent years there has been growing interest in the use of artificial materials, in particular, materials formed from polymers, for use in implantable devices that come into contact with bodily tissues or fluids particularly blood. Some examples of such devices are artificial heart valves, stents, and vascular prosthesis. Some medical devices such as implantable stents which are fabricated from a metal have been problematic in fracturing or failing after implantation. Moreover, certain other implantable devices made from polymers have exhibited problems such as increased wall thickness to prevent or inhibit fracture or failure. However, stents having reduced wall thickness are desirable particularly for treating arterial diseases.

Because many polymeric implants such as stents are fabricated through processes such as extrusion or injection molding, such methods typically begin the process by starting with an inherently weak material. In the example of a polymeric stent, the resulting stent can have imprecise geometric tolerances as well as reduced wall thicknesses which can make these stents susceptible to brittle fracture.

A stent which is susceptible to brittle fracture is generally undesirable because of its limited ability to collapse for intravascular delivery as well as its limited ability to expand for placement or positioning within a vessel. Moreover, such polymeric stents also exhibit a reduced level of strength. Brittle fracture is particularly problematic in stents as placement of a stent onto a delivery balloon or within a delivery sheath imparts a substantial amount of compressive force in the material comprising the stent. A stent made of a brittle material can crack or have a very limited ability to collapse or expand without failure. Thus, a certain degree of malleability is desirable for a stent to expand, deform, and maintain its position securely within the vessel.

Certain indications, such as peripheral arterial disease, affects millions of people where the superficial femoral artery (SFA) is commonly involved. Stenosis or occlusion of the SFA is a common cause of many symptoms such as claudication and is often part of critical limb ischemia. Although interventional therapy for SFA diseases using Nitinol stents is increasing, the SFA poses particular problems with respect to stent implantation because the SFA typically elongates and foreshortens with movement, can be externally compressed, and is subject to flexion. Limitations of existing stents include, e.g., insufficient radial strength to withstand elastic recoil and external compression, kinking, and fracture.

Because of such limitations, stent fractures have been reported to occur in the iliac, popliteal, subclavian, pulmonary, renal, and coronary arteries. However, it is suspected that these fractures can occur at a higher rate in the SFA than the other locations. For example, because the SFA can undergo dramatic non-pulsatile deformations (e.g., axial compression and extension, radial compression, bending, torsion, etc.) such as during hip and knee flexion causing significant SFA shortening and elongation and because the SFA has a tendency to develop long, diffuse, disease states with calcification requiring the use of multiple overlapping stents, stent placement, maintenance, and patency is difficult. Moreover, overlapping of adjacent stents cause metal-to-metal stress points that can initiate a stent fracture.

Accordingly, there is a need for an implantable stent that is capable of withstanding the dynamic loading conditions of the SFA and other similar environments.

SUMMARY

When a stent is placed into a vessel, particularly vessels such as the superficial femoral artery (SFA), iliac, popliteal, subclavian, pulmonary, renal, or the coronary arteries, the stent's ability to bend and compress is reduced. Moreover, such vessels typically undergo a great range of motion requiring stents implanted within these vessels to have an axial flexibility which allows for its compliance with the arterial movement without impeding or altering the physiological axial compression and bending normally found with positional changes.

A composite stent structure having one or more layers of bioabsorbable polymers can be fabricated with the desired characteristics for implantation within these vessels. Each layer can have a characteristic that individually provides a certain aspect of mechanical behavior to the stent such that the aggregate layers form a composite polymeric stent structure capable of withstanding complex, multi-axial loading conditions imparted by an anatomical environment such as the SFA.

Generally, a tubular substrate can be constructed by positioning one or more high-strength bioabsorbable polymeric ring structures spaced apart from one another along a longitudinal axis. The ring structures can be connected to one another by one or more layers of polymeric substrates, such as bioabsorbable polymers which are also elastomeric. Such a structure is made of several layers of bioabsorbable polymers with each layer having a specific property that positively affects certain aspects of the mechanical behavior of the stent and all layers collectively as a composite polymeric material creates a structure capable of withstanding the complex, multi-axial loading conditions of an anatomical environment such as the SFA.

A number of casting processes can be utilized to develop substrates, such as cylindrically shaped substrates having a relatively high level of geometric precision and mechanical strength for forming the aforementioned ring structures. These polymeric substrates can then be machined using any number of processes (e.g., high-speed laser sources, mechanical machining, etc.) to create devices such as stents having a variety of geometries for implantation within a patient, such as the peripheral or coronary vasculature of the patient.

An example of such a casting process is to utilize a dip-coating process. The utilization of dip-coating results in polymeric substrates which are able to retain the inherent properties of the starting materials. This in turn results in polymeric substrates having a relatively high radial strength which is retained through any additional manufacturing processes for implantation. Additionally, dip-coating also allows for the creation of polymeric substrates having multiple layers.

In using dip-coating to form the polymeric substrate, one or more high molecular weight biocompatible and/or bioabsorbable polymers can be selected for forming upon a mandrel. The one or more polymers can be dissolved in a compatible solvent in one or more corresponding containers such that the appropriate solution can be placed under the mandrel. The substrate can be formed to have multiple layers overlaid upon one another such that the substrate has a first layer of a first polymer, a second layer of a second polymer, and so on depending upon the desired structure and properties of the substrate. Thus, the various solutions and containers can be replaced beneath the mandrel between dip-coating operations in accordance with the desired layers to be formed upon the substrate such that the mandrel can be dipped sequentially into the appropriate polymeric solution.

Parameters such as the number of times the mandrel is immersed, the sequence and direction of dipping, the duration of each immersion, the delay time between each immersion, or the drying or curing time between dips can each be controlled to yield a substrate having the desired mechanical characteristics. For example, the dip-coating process can be used to form a polymeric substrate having half the wall thickness of a substrate formed from extrusion while retaining an increased level of strength in the polymeric substrate.

The immersion times as well as the drying times can be uniform between each immersion or can be varied as determined by the desired properties of the resulting substrate. Moreover, the substrate can be placed in an oven or dried at ambient temperatures between each immersion or after the final immersion to attain a predetermined level of crystals (e.g., 60%) and a predetermined level of amorphous polymeric regions (e.g., 40%). Each of the layers overlaid upon one another during the dip-coating process can be tightly adhered to one another and the wall thicknesses and mechanical properties of each polymer can be retained in their respective layer with no limitation on the molecular weight and/or crystalline structure of the polymers utilized.

Dip-coating can also be used to impart an orientation between layers (e.g., linear orientation by dipping, radial orientation by spinning the mandrel, etc.) to further enhance the mechanical properties of the formed substrate. As radial strength is a desirable attribute of stent design, post-processing of the formed substrate can be accomplished to impart such attributes. Typically, polymeric stents suffer from having relatively thick walls to compensate for the lack of radial strength, and this, in turn, reduces flexibility, impedes navigation, and reduces arterial luminal area immediately post implantation. Post-processing can also help to prevent material creep and recoil which are problems typically associated with polymeric stents. Creep is a time-dependent permanent deformation that occurs to a specimen under stress, typically under elevated temperatures.

For post-processing, a predetermined amount of force can be applied to the substrate where such a force can be generated by a number of different methods. One method is by utilizing an expandable pressure vessel placed within the substrate. Another method is by utilizing a braid structure, such as a braid made from a super-elastic or shape memory alloy, such as Nitinol, to increase in size and to apply the desirable degree of force against the interior surface of the substrate.

Yet another method can apply the expansion force by application of a pressurized inert gas such as nitrogen within the substrate lumen. A completed substrate can be placed inside a molding tube which has an inner diameter that is larger than the cast cylinder. A distal end or distal portion of the cast cylinder can be clamped or otherwise closed and a pressure source can be coupled to a proximal end of the cast cylinder. The entire assembly can be positioned over a nozzle which applies heat to either the length of the cast cylinder or to a portion of cast cylinder. The increase in diameter of the cast cylinder can thus realign the molecular orientation of the cast cylinder to increase its radial strength. After the diameter has been increased, the cast cylinder can be cooled.

The molecular weight of a polymer is typically one of the factors in determining the mechanical behavior of the polymer. With an increase in the molecular weight of a polymer, there is generally a transition from brittle to ductile failure. A mandrel can be utilized to cast or dip-coat the polymeric substrate. Further examples of high-strength bioabsorbable polymeric substrates formed via dip-coating processes are described in further detail in U.S. patent application Ser. No. 12/143,659 filed Jun. 20, 2008, which is incorporated herein by reference in its entirety.

The substrate can also be machined, e.g., using laser ablation processes, to produce stents with suitable geometries for particular applications. The composite stent structure can have a relatively high radial strength as provided by the polymeric ring structures while the polymeric portions extending between the adjacent ring structures can allow for elastic compression and extension of the stent structure axially as well as torsionally when axial and rotational stresses are imparted by ambulation and positional changes from the vessel upon the stent structure.

Also disclosed is a bioabsorbable composite stent structure comprising bioabsorbable polymeric ring structures and one or more interconnecting struts which extend between and couple adjacent ring structures. The polymeric ring structures can retain a molecular weight and mechanical strength of a starting substrate. The ring structures can be formed at a first diameter and be radially compressible to a smaller second diameter. The ring structures can also be re-expandable to the first diameter. The ring structures can be separated from one another and comprise a base polymeric layer. The base polymeric layer can be a bioabsorbable polymeric substrate formed via a dip-coating process.

The one or more interconnecting struts can extend between and couple adjacent ring structures. Each of the interconnecting struts can have a width which is less than a circumference of one of the ring structures. The interconnecting struts can be formed from or comprise a polymer blend or co-polymer of poly-L-lactide (PLLA) and an elastomeric polymer.

The adjacent ring structures can be axially and rotationally movable relative to one another via the interconnecting struts. The one or more interconnecting struts can also be bioabsorbable such that the entire composite stent structure can be bioabsorbable.

In one variation, the elastomeric polymer can be or comprise polycaprolactone (PCL). The PCL can be about 1% to about 10% of the polymer blend or co-polymer. In other variations, the PCL can be about 1% to about 50% of the polymer blend or co-polymer. In certain variations, the polymer blend or co-polymer can have a glass transition temperature between 50° C. and 65° C.

The ring structures can be spaced closer to one another along a first portion than along a second portion of the stent structure. A terminal ring structure can be relatively more flexible than a remainder of the ring structures.

Another bioabsorbable composite stent structure is disclosed comprising bioabsorbable polymeric ring structures and a plurality of interconnecting struts which extend between and couple adjacent ring structures. The polymeric ring structures can retain a molecular weight and mechanical strength of a starting substrate. The ring structures can be formed at a first diameter and be radially compressible to a smaller second diameter. The ring structures can also be re-expandable to the first diameter. The ring structures can be separated from one another and comprise a base polymeric layer. The base polymeric layer can be a bioabsorbable polymeric substrate formed via a dip-coating process.

The plurality of interconnecting struts can extend between and couple adjacent ring structures. Each of the interconnecting struts can have a width which is less than a circumference of one of the ring structures. The plurality of interconnecting struts can be formed from or comprise a polymer blend or co-polymer of poly-L-lactide (PLLA) and an elastomeric polymer. The plurality of interconnecting struts can be positioned along a length of the composite stent structure in a circumferentially alternating manner between immediately adjacent ring structures.

The adjacent ring structures can be axially and rotationally movable relative to one another via the interconnecting struts. The one or more interconnecting struts can also be bioabsorbable such that the entire composite stent structure can be bioabsorbable.

The elastomeric polymer making up part of the polymer blend or co-polymer can be or comprise polycaprolactone (PCL). The PCL can be about 1% to about 10% of the polymer blend or co-polymer. In other variations, the PCL can be about 1% to about 50% of the polymer blend or co-polymer. In certain variations, the polymer blend or co-polymer can have a glass transition temperature between 50° C. and 65° C.

The ring structures can be spaced closer to one another along a first portion than along a second portion of the stent structure. A terminal ring structure can be relatively more flexible than a remainder of the ring structures.

Yet another bioabsorbable composite stent structure is disclosed comprising bioabsorbable polymeric ring structures and one or more interconnecting struts which extend between and couple adjacent ring structures. The polymeric ring structures can retain a molecular weight and mechanical strength of a starting substrate. The ring structures can be formed at a first diameter and be radially compressible to a smaller second diameter. The ring structures can also be re-expandable to the first diameter. The ring structures can be separated from one another and comprise a base polymeric layer. The base polymeric layer can be a bioabsorbable polymeric substrate formed via a dip-coating process.

The one or more interconnecting struts can extend between and couple adjacent ring structures. Each of the interconnecting struts can have a width which is less than a circumference of one of the ring structures. The interconnecting struts can be formed from or comprise a polymer blend or co-polymer of poly-L-lactide (PLLA) and an elastomeric polymer. The one or more interconnecting struts can be more elastic than the ring structures.

The adjacent ring structures can be axially and rotationally movable relative to one another via the interconnecting struts. The one or more interconnecting struts can also be bioabsorbable such that the entire composite stent structure can be bioabsorbable.

The elastomeric polymer making up part of the polymer blend or co-polymer can be or comprise polycaprolactone (PCL). The PCL can be about 1% to about 10% of the polymer blend. In other variations, the PCL can be about 1% to about 50% of the polymer blend or co-polymer. In certain variations, the polymer blend or co-polymer can have a glass transition temperature between 50° C. and 65° C.

The ring structures can be spaced closer to one another along a first portion than along a second portion of the stent structure. A terminal ring structure can be relatively more flexible than a remainder of the ring structures.

BRIEF DESCRIPTION OF THE DRAWINGS

FIGS. 3A to 3B illustrate partial cross-sectional side views of a portion of an example multi-layer polymeric substrate disclosed herein.

FIG. 3C illustrates a cross-sectional end view of a portion of an example multi-layer polymeric substrate disclosed herein.

DETAILED DESCRIPTION

When a stent is placed into a vessel such as the superficial femoral artery (SFA), iliac, popliteal, subclavian, pulmonary, renal, or coronary arteries, the stent's ability to bend and compress is reduced. Moreover, such vessels typically undergo a great range of motion requiring stents implanted within these vessels to have an axial flexibility which allows for the stent to comply with certain vessel movements without impeding or altering the physiological compression and bending of such vessels.

A composite stent structure having one or more layers of bioabsorbable polymers can be fabricated with the desired characteristics for implantation within these vessels. Each layer can have a characteristic that individually provides a certain aspect of mechanical behavior to the stent such that the aggregate layers form a composite polymeric stent structure capable of withstanding complex, multi-axial loading conditions imparted by an anatomical environment such as the SFA.

Generally, a tubular substrate can be constructed by positioning one or more high-strength bioabsorbable polymeric ring structures spaced apart from one another along a longitudinal axis. The ring structures can be connected to one another by one or more layers of polymeric substrates, such as bioabsorbable polymers which are also elastomeric. The substrate can also be machined, e.g., using laser ablation processes, to produce stents with suitable geometries for particular applications. The composite stent structure can have a relatively high radial strength as provided by the polymeric ring structures while the polymeric portions extending between the adjacent ring structures can allow for elastic compression and extension of the stent structure axially as well as torsionally when axial and rotational stresses are imparted by ambulation and positional changes from the vessel upon the stent structure.

In manufacturing the polymeric ring structures from polymeric materials such as biocompatible and/or biodegradable polymers (e.g., poly-L-lactic acid (PLLA) 2.4, PLLA 4.3, PLLA 8.4, PLA, PLGA, etc.), a number of casting processes can be utilized to develop substrates, e.g., cylindrically shaped substrates, having a relatively high level of geometric precision and mechanical strength. A high-strength tubular material which exhibits a relatively high degree of ductility can be fabricated utilizing such polymers having a relatively high molecular weight These polymeric substrates can then be machined using any number of processes (e.g., high-speed laser sources, mechanical machining, etc.).

Figure 1A:
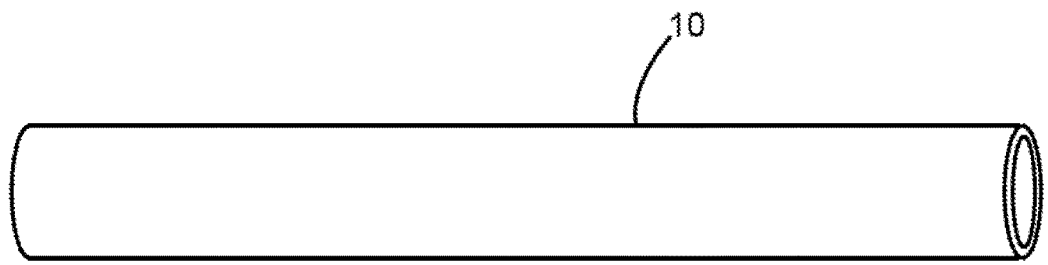
FIG. 1A illustrates an example of a polymeric substrate having one or more layers formed by dip coating processes creating a substrate having a relatively high radial strength and ductility.

An example of such a casting process is to utilize a dip-coating process. The utilization of dip-coating to create a base polymeric substrate 10, as illustrated in FIG. 1A, having such desirable characteristics results in substrates 10 which are able to retain the inherent properties of the starting materials. This, in turn, results in substrates 10 having a relatively high radial strength which is mostly retained through any additional manufacturing processes for implantation. Additionally, dip-coating the polymeric substrate 10 also allows for the creation of substrates having multiple layers. The multiple layers can be formed from the same or similar materials or they can be varied to include any member of additional agents, such as one or more drugs for treatment of the vessel, as described in further detail below. Moreover, the variability of utilizing multiple layers for the substrate can allow one to control other parameters, conditions, or ranges between individual layers such as varying the degradation rate between layers while maintaining the intrinsic molecular weight and mechanical strength of the polymer at a high level with minimal degradation of the starting materials.

Because of the retention of molecular weight and mechanical strength of the starting materials via the casting or dip-coating process, polymeric substrates 10 can be formed which enable the fabrication of devices such as stents with reduced wall thickness which is highly desirable for the treatment of arterial diseases. Furthermore, these processes can produce structures having precise geometric tolerances with respect to wall thicknesses, concentricity, diameter, etc.

One mechanical property in particular which is generally problematic for polymeric stents formed from polymeric substrates is failure via brittle fracture of the device when placed under stress within the patient body. It is generally desirable for polymeric stents to exhibit ductile failure under an applied load rather via brittle failure, especially during delivery and deployment of a polymeric stent from an inflation balloon or constraining sheath. Further examples of high-strength bioabsorbable polymeric substrates formed via dip-coating processes are described in further detail in U.S. patent application Ser. No. 12/143,659 filed Jun. 20, 2008, which is incorporated herein by reference in its entirety.

Figure 1B:
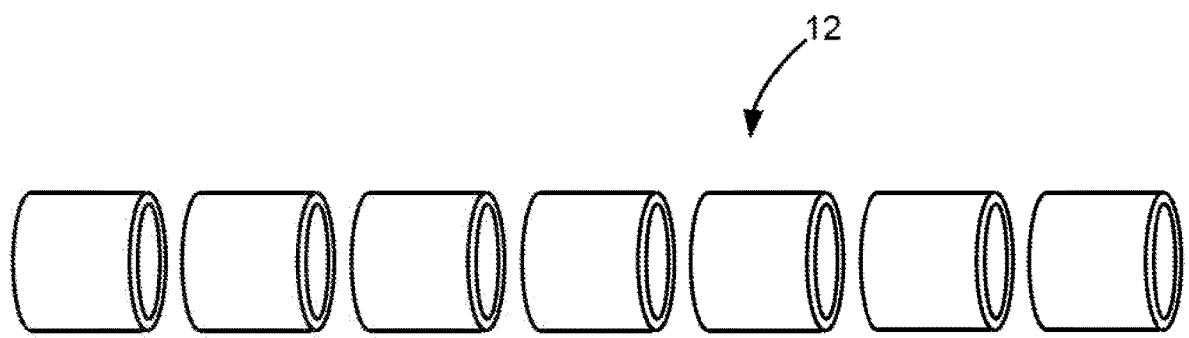
FIG. 1B illustrates an example the formed polymeric substrate cut or machined into a number of circular ring-like structures.

Such dip-coating methods can be utilized to create polymeric substrates such as base polymeric substrate 10, which can then be cut into a plurality of polymeric ring structures 12, as shown in FIG. 1B. These ring structures can have a width which varies depending upon the application and vessel and can range generally from 1 mm to 10 mm in width. Moreover, because the initial polymeric substrate or base polymeric substrate 10 is formed upon a mandrel, substrate 10 and the resulting ring structures 12 can be formed to have an initial diameter ranging generally from 2 mm to 10 mm.

Figure 2A:
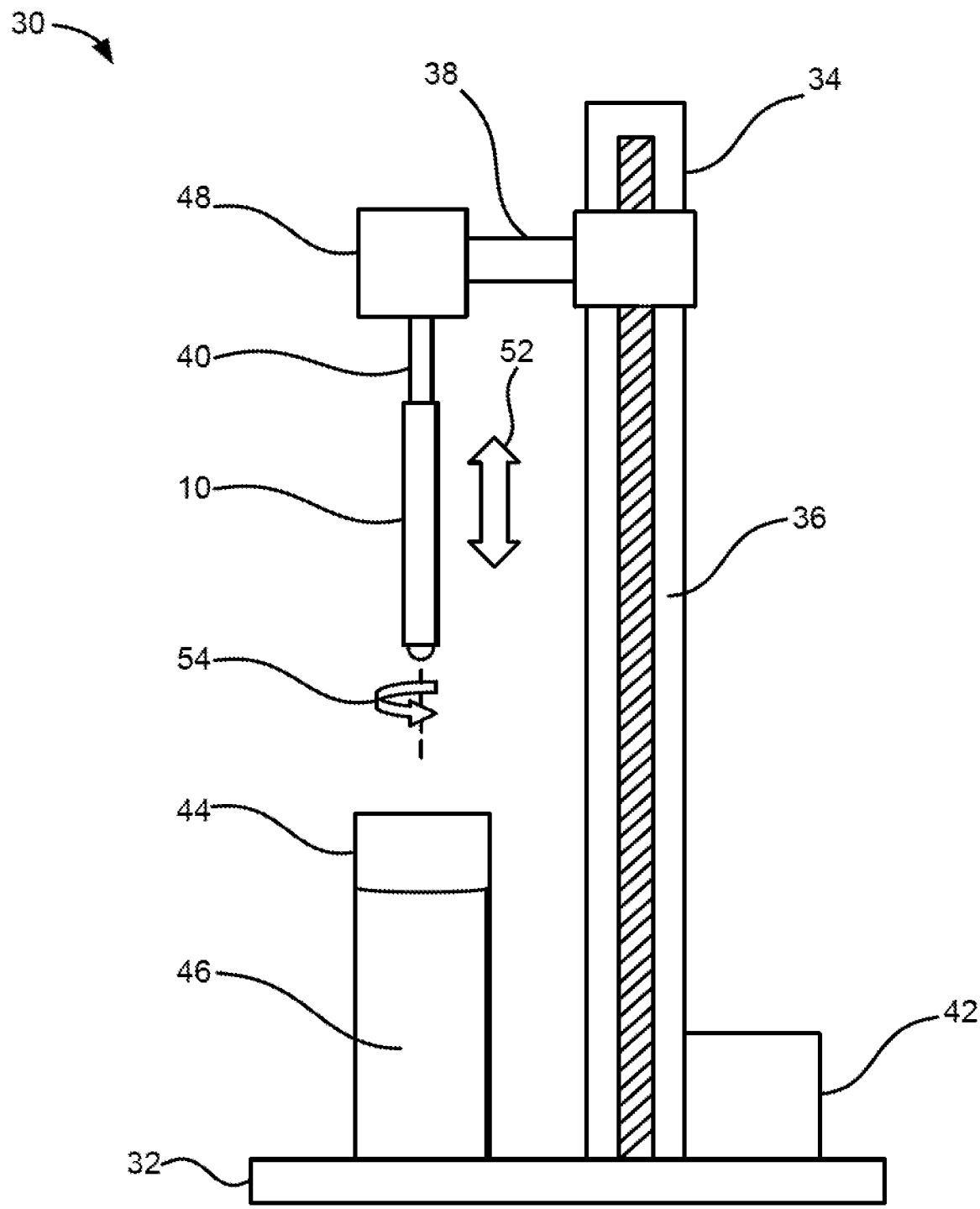
FIG. 2A illustrates an example of a dip-coating assembly or device which can be utilized to form any variation of the polymeric substrates disclosed herein.

An example of a dip-coating assembly 30 which can be utilized to cast or dip-coat the polymeric substrate is illustrated in the side view of FIG. 2A. The dip-coating assembly 30 can comprise a base 32 supporting a column 34 which houses a drive column 36 and a bracket arm 38. Motor 42 can urge drive column 36 vertically along column 34 to move bracket arm 38 accordingly. Mandrel 40 can be attached to bracket arm 38 above container 44 which can be filled with a polymeric solution 46 (e.g., PLLA, PLA, PLGA, etc.) into which mandrel 40 can be dipped via a linear motion 52. The one or more polymers can be dissolved in a compatible solvent in one or more corresponding containers 44 such that the appropriate solution can be placed under mandrel 40. An optional motor 48 can be mounted along bracket arm 38 or elsewhere along assembly 30 to impart an optional rotational motion 54 to mandrel 40 and the substrate 10 formed along mandrel 40 to impart an increase in the circumferential strength of substrate 10 during the dip-coating process, as described in further detail below.

The assembly 30 can be isolated on a vibration-damping or vibrationally isolated table to ensure that the liquid surface held within container 44 remains completely undisturbed to facilitate the formation of a uniform thickness of polymer material along mandrel 40 and/or substrate 10 with each deposition The entire assembly 30 or just a portion of the assembly such as the mandrel 40 and polymer solution can be placed in an inert environment such as a nitrogen gas environment while maintaining a very low relative humidity (RH) level, e.g., less than 30% RH, and appropriate dipping temperature, e.g., at least 20° C. below the boiling point of the solvent within container 44 so as to ensure adequate bonding between layers of the dip-coated substrate. Multiple mandrels can also be mounted along bracket arm 38 or directly to column 34.

The mandrel 40 can be sized appropriately and define a cross-sectional geometry to impart a desired shape and size to the substrate 10. Mandrel 40 can be generally circular in cross section although geometries can be utilized as desired. In one example, mandrel 40 can define a circular geometry having a diameter ranging from 1 mm to 20 mm to form a polymeric substrate having a corresponding inner diameter. Moreover, mandrel 40 can be made generally from various materials which are suitable to withstand dip-coating processes, e.g., stainless steel, copper, aluminum, silver, brass, nickel, titanium, etc. The length of mandrel 40 that is dipped into the polymer solution can be optionally limited in length by, e.g., 50 cm, to ensure that an even coat of polymer is formed along the dipped length of mandrel 40 to limit the effects of gravity during the coating process. Mandrel 40 can also be made from a polymeric material which is lubricious, strong, has good dimensional stability, and is chemically resistant to the polymer solution utilized for dip-coating, e.g., fluoropolymers, polyacetal, polyester, polyamide, polyacrylates, etc.

Moreover, mandrel 40 can be made to have a smooth surface for the polymeric solution to form upon. In other variations, mandrel 40 can define a surface that is coated with a material such as polytetrafluoroethylene to enhance removal of the polymeric substrate formed thereon. In yet other variations, mandrel 40 can be configured to define any number of patterns over its surface, e.g., either over its entire length or just a portion of its surface, that can be mold-transferred during the dip-coating process to the inner surface of the first layer of coating of the dip-coated substrate tube. The patterns can form raised or depressed sections to form various patterns such as checkered, cross-hatched, cratered, etc. that can enhance endothelialization with the surrounding tissue after the device is implanted within a patient, e.g., within three months or of implantation.

The direction that mandrel 40 is dipped within polymeric solution 46 can also be alternated or changed between layers of substrate 10. In forming substrates having a length ranging from, e.g., 1 cm to 40 cm or longer, substrate 10 can be removed from mandrel 40 and replaced onto mandrel 40 in an opposite direction before the dipping process is continued. Alternatively, mandrel 40 can be angled relative to bracket arm 38 and/or polymeric solution 46 during or prior to the dipping process.

Figure 2B:
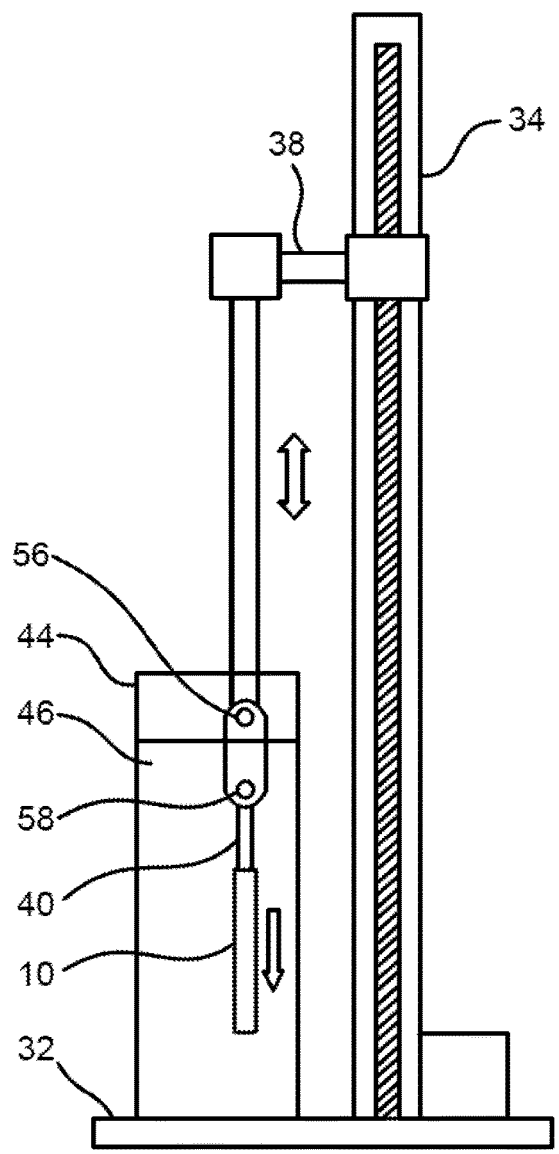
FIG. 2B illustrates another example of a dip-coating assembly or device which can be utilized to form any variation of the polymeric substrates disclosed herein.
Figure 2C:
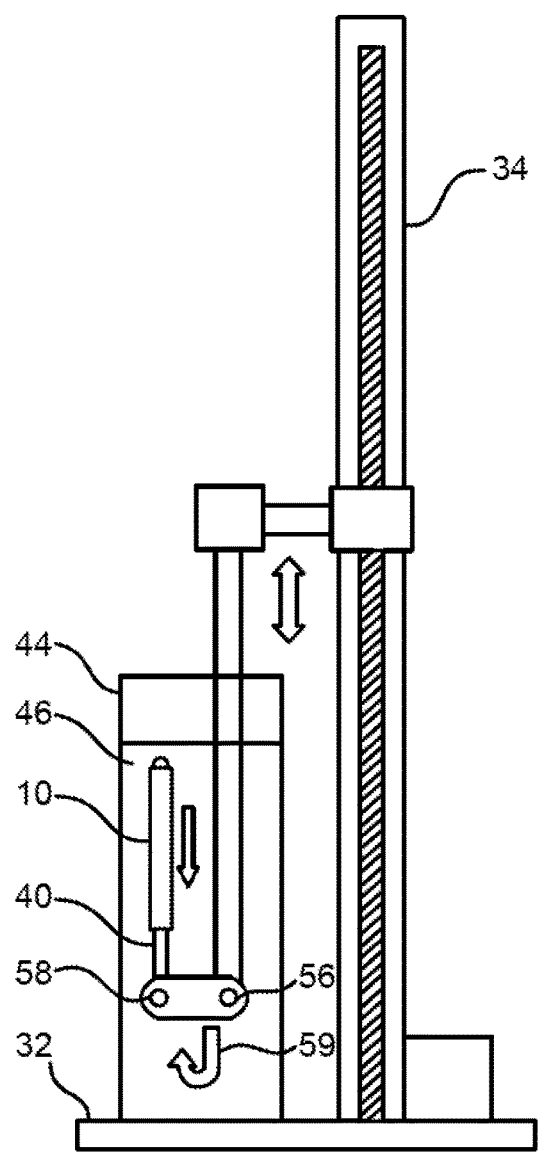
FIG. 2C illustrates yet another example of a dip-coating assembly or device which can be utilized to form any variation of the polymeric substrates disclosed herein.

This can also be accomplished in yet another variation by utilizing a dipping assembly as illustrated in FIGS. 2B and 2C to achieve a uniform wall thickness throughout the length of the formed substrate 10 per dip. For instance, after 1 to 3 coats are formed in a first dipping direction, additional layers formed upon the initial layers can be formed by dipping mandrel 40 in a second direction opposite to the first dipping direction, e.g., angling the mandrel 40 anywhere up to 180° from the first dipping direction. This can be accomplished in one example through the use of one or more pivoting linkages 56, 58 connecting mandrel 40 to bracket arm 38, as illustrated. The one or more linkages 56, 58 can maintain mandrel 40 in a first vertical position relative to solution 46 to coat the initial layers of substrate 10, as shown in FIG. 2B. Linkages 56, 58 can then be actuated to reconfigure mandrel 40 from its first vertical position to a second vertical position opposite to the first vertical position, as indicated by direction 59 in FIG. 2C. With repositioning of mandrel 40 complete, the dipping process can be resumed by dipping the entire linkage assembly along with mandrel 40 and substrate 10. In this manner, neither mandrel 40 nor substrate 10 needs to be removed and thus eliminates any risk of contamination. Linkages 56, 58 can comprise any number of mechanical or electromechanical pivoting and/or rotating mechanisms as known in the art.

Dipping mandrel 40 and substrate 10 in different directions can also enable the coated layers to have a uniform thickness throughout from its proximal end to its distal end to help compensate for the effects of gravity during the coating process. These values are intended to be illustrative and are not intended to be limiting in any manner. Any excess dip-coated layers on the linkages 56, 58 can simply be removed from mandrel 40 by breaking the layers. Alternating the dipping direction can also result in the polymers being oriented alternately which can reinforce the tensile strength in the axial direction of the dip coated tubular substrate 10.

With dip-coating assembly 30, one or more high molecular weight biocompatible and/or bioabsorbable polymers can be selected for forming upon mandrel 40. Examples of polymers which can be utilized to form the polymeric substrate can include, but is not limited to, polyethylene, polycarbonates, polyamides, polyesteramides, polyetheretherketone, polyacetals, poly ketals, polyurethane, polyolefin, or polyethylene terephthalate and degradable polymers, for example, polylactide (PLA) including poly-L-lactide (PLLA), poly-glycolide (PGA), poly(lactide-co-glycolide) (PLGA) or polycaprolactone, caprolactones, polydioxanones, poly anhydrides, poly orthocarbonates, polyphosphazenes, chitin, chitosan, poly(amino acids), and polyorthoesters, and copolymers, terpolymers and combinations and mixtures thereof.

Other examples of suitable polymers can include synthetic polymers, for example, oligomers, homopolymers, and co-polymers, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyls acetate; polymers formed of ethylene, propylene, and tetrafluoroethylene. Further examples can include nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketones.

Examples of biodegradable polymers which can be used for dip-coating process are polylactide (PLA), polyglycolide (PGA), poly(lactide-co-glycolide) (PLGA), poly-ε-caprolactone (PCL), polydioxanone, polyanhydride, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and polyphosphazene, and copolymers, terpolymers and combinations and mixtures thereof. There are also a number of biodegradable polymers derived from natural sources such as modified polysaccharides (e.g., cellulose, chitin, chitosan, or dextran) or modified proteins (e.g., fibrin or casein).

Other examples of suitable polymers can include synthetic polymers, for example, oligomers, homopolymers, and co-polymers, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyls acetate; polymers formed of ethylene, propylene, and tetrafluoroethylene. Further examples can include nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketones.

These examples of polymers which can be utilized for forming the substrate are not intended to be limiting or exhaustive but are intended to be illustrative of potential polymers which can be used. As the substrate can be formed to have one or more layers overlaid upon one another, the substrate can be formed to have a first layer of a first polymer, a second layer of a second polymer, and so on depending upon the desired structure and properties of the substrate. Thus, the various solutions and containers can be replaced beneath mandrel 40 between dip-coating operations in accordance with the desired layers to be formed on the substrate such that the mandrel 40 can be dipped sequentially into the appropriate polymeric solution.

Depending upon the desired wall thickness of the formed substrate, the mandrel 40 can be dipped into the appropriate solution as determined by the number of times the mandrel 40 is immersed, the duration of time of each immersion within the solution, as well as the delay time between each immersion or the drying or curing time between dips. Additionally, parameters such as the dipping and/or withdrawal rate of the mandrel 40 from the polymeric solution can also be controlled to range from, e.g., 5 mm/min to 1000 mm/min. Formation via the dip-coating process can result in a polymeric substrate having half the wall thickness while retaining an increased level of strength in the substrate as compared to an extruded polymeric structure. For example, to form a substrate having a wall thickness of, e.g., 200 μm, built up of multiple layers of polylactic acid, mandrel 40 can be dipped between, e.g., 2 to 20 times or more, into the polymeric solution with an immersion time ranging from, e.g., 15 seconds (or less) to 240 minutes (or more). Moreover, the substrate and mandrel 40 can be optionally dried or cured for a period of time ranging from, e.g., 15 seconds (or less) to 60 minutes (or more) between each immersion. These values are intended to be illustrative and are not intended to be limiting in any manner.

Aside from utilizing materials which are relatively high in molecular weight, another parameter which can be considered in further increasing the ductility of the material is its crystallinity, which refers to the degree of structural order in the polymer. Such polymers can contain a mixture of crystalline and amorphous regions such that reducing the percentage of the crystalline regions in the polymer can further increase the ductility of the material. Polymeric materials not only having a relatively high molecular weight but also having a relatively low crystalline percentage can be utilized in the processes described herein to form a desirable tubular substrate.

The following Table 1 show examples of various polymeric materials (e.g., PLLA IV 8.28 and PDLLA 96/4) to illustrate the molecular weights of the materials in comparison to their respective crystallinity percentage. The glass transition temperature, $T_g$, as well as melting temperature, $T_m$, are given as well. An example of PLLA IV 8.28 is shown illustrating the raw resin and tube form as having the same molecular weight, $M_w$, of $1.70 \times 10^6$ gram/mol. However, the crystallinity percentage of PLLA IV 8.28 Resin is 61.90% while the corresponding Tube form is 38.40%. Similarly for PDLLA 96/4, the resin form and tube form each have a molecular weight, $M_w$, of $9.80 \times 10^5$ gram/mol; however, the crystallinity percentages are 46.20% and 20.90%, respectively.

TABLE 1

Various polymeric materials and their respective crystallinity percentages.

| Material | $T_g$ (° C.) | $T_m$ (° C.) | Crystallinity (%) | $M_w$ (gram/mol) |
| --- | --- | --- | --- | --- |
| PLLA IV8.28 Resin | 72.5 | 186.4 | 61.90% | $1.70 \times 10^6$ |
| PLLA IV8.28 Tubes | 73.3 | 176.3 | 38.40% | $1.70 \times 10^6$ |
| PDLLA 96/4 Resin | 61.8 | 155.9 | 46.20% | $9.80 \times 10^5$ |
| PDLLA 96/4 Tubes | 60.3 | 146.9 | 20.90% | $9.80 \times 10^5$ |

As the resin is dip coated to form the tubular substrate through the methods described herein, the drying procedures and processing help to preserve the relatively high molecular weight of the polymer from the starting material and throughout processing to substrate and stent formation. Moreover, the drying process in particular can facilitate the formation of desirable crystallinity percentages, as described above.

Aside from the crystallinity of the materials, the immersion times as well as drying times can be uniform between each immersion or they can be varied as determined by the desired properties of the resulting substrate. Moreover, the substrate can be placed in an oven or dried at ambient temperature between each immersion or after the final immersion to attain a predetermined level of crystals, e.g., 60%, and a level of amorphous polymeric structure, e.g., 40%. Each of the layers overlaid upon one another during the dip-coating process can be tightly adhered to one another and the mechanical properties of each polymer are retained in their respective layer with no limitation on the molecular weight of the polymers utilized.

Varying the drying conditions of the materials can also be controlled to effect desirable material parameters. The polymers can be dried at or above the glass transition temperature (e.g., 10° to 20° C. above the glass transition temperature, $T_g$) of the respective polymer to effectively remove any residual solvents from the polymers to attain residual levels of less than 100 ppm, e.g., between 20 to 100 ppm. Positioning of the polymer substrate when drying is another factor which can be controlled as affecting parameters, such as geometry, of the tube. For instance, the polymer substrate can be maintained in a drying position such that the substrate tube is held in a perpendicular position relative to the ground such that the concentricity of the tubes is maintained. The substrate tube can be dried in an oven at or above the glass transition temperature, as mentioned, for a period of time ranging anywhere from, e.g., 10 days to 30 days or more. However, prolonged drying for a period of time, e.g., greater than 40 days, can result in thermal degradation of the polymer material.

Additionally and/or optionally, a shape memory effect can be induced in the polymer during drying of the substrate. For instance, a shape memory effect can be induced in the polymeric tubing to set the tubular shape at the diameter that was formed during the dip-coating process. An example of this is to form a polymeric tube by a dip-coating process described herein at an outer diameter of 5 mm and subjecting the substrate to temperatures above its glass transition temperature, $T_g$. At its elevated temperature, the substrate can be elongated, e.g., from a length of 5 cm to 7 cm, while the outer diameter of the substrate is reduced from about 5.0 mm to about 3.0 mm. Of course, these examples are merely illustrative and the initial diameter can generally range anywhere from, e.g., 3 mm to 9 mm, and the reduced diameter can generally range anywhere from, e.g., 1.5 mm to 5 mm, provided the reduced diameter is less than the initial diameter.

Once lengthened and reduced in diameter, the substrate can be quenched or cooled in temperature to a sub-$T_g$ level, e.g., about 20° C. below its $T_g$, to allow for the polymeric substrate to transition back to its glass state. This effectively imparts a shape memory effect of self-expansion to the original diameter of the substrate. When such a tube (or stent formed from the tubular substrate) is compressed or expanded to a smaller or larger diameter and later exposed to an elevated temperature, over time the tube (or stent) can revert to its original 5 mm diameter. This post-processing can also be useful for enabling self-expansion of the substrate after a process like laser cutting (e.g., when forming stents or other devices for implantation within the patient) where the substrate tube is typically heated to its glass transition temperature, $T_g$.

An example of a substrate having multiple layers is illustrated in FIGS. 3A and 3B which show partial cross-sectional side views of an example of a portion of a multi-layer polymeric substrate formed along mandrel 40 and the resulting substrate. Substrate 10 can be formed along mandrel 40 to have a first layer 60 formed of a first polymer, e.g., poly(l-lactide). After the formation of first layer 60, an optional second layer 62 of polymer, e.g., poly(L-lactide-co-glycolide), can be formed upon first layer 60. Yet another optional third layer 64 of polymer, e.g., poly(d,l-lactide-co-glycolide), can be formed upon second layer 62 to form a resulting substrate defining a lumen 66 therethrough which can be further processed to form any number of devices, such as a stent. One or more of the layers can be formed to degrade at a specified rate or to elute any number of drugs or agents.

An example of this is illustrated in the cross-sectional end view of FIG. 3C, which shows an exemplary substrate having three layers 60, 62, 64 formed upon one another, as above. In this example, first layer 60 can have a molecular weight of $M_{n1}$, second layer 62 can have a molecular weight of $M_{n2}$, and third layer 64 can have a molecular weight of $M_{n3}$. A stent fabricated from the tube can be formed such that the relative molecular weights are such where $M_{n1} > M_{n2} > M_{n3}$ to achieve a preferential layer-by-layer degradation through the thickness of the tube beginning with the inner first layer 60 and eventually degrading to the middle second layer 62 and finally to the outer third layer 64 when deployed within the patient body. Alternatively, the stent can be fabricated where the relative molecular weights are such where $M_{n1} < M_{n2} < M_{n3}$ to achieve a layer-by-layer degradation beginning with the outer third layer 64 and degrading towards the inner first layer 60. This example is intended to be illustrative and fewer than or more than three layers can be utilized in other examples. Additionally, the molecular weights of each respective layer can be altered in other examples to vary the degradation rates along different layers, if so desired.

Moreover, any one or more of the layers can be formed to impart specified mechanical properties to the substrate 10 such that the composite mechanical properties of the resulting substrate 10 can specifically tuned or designed. Additionally, although three layers are illustrated in this example, any number of layers can be utilized depending upon the desired mechanical properties of the substrate 10.

Moreover, as multiple layers can be overlaid one another in forming the polymeric substrate, specified layers can be designated for a particular function in the substrate. For example, in substrates which are used to manufacture polymeric stents, one or more layers can be designed as load-bearing layers to provide structural integrity to the stent while certain other layers can be allocated for drug-loading or eluting. Those layers which are designated for structural support can be formed from high-molecular weight polymers. e.g., PLLA or any other suitable polymer described herein, to provide a high degree of strength by omitting any drugs as certain pharmaceutical agents can adversely affect the mechanical properties of polymers. Those layers which are designated for drug-loading can be placed within, upon, or between the structural layers.

Additionally, multiple layers of different drugs can be loaded within the various layers. The manner and rate of drug release from multiple layers can depend in part upon the degradation rates of the substrate materials. For instance, polymers which degrade relatively quickly can release their drugs layer-by-layer as each successive layer degrades to expose the next underlying layer. In other variations, drug release can typically occur from a multilayer matrix via a combination of diffusion and degradation. In one example, a first layer can elute a first drug for, e.g., the first 30 to 40 days after implantation. Once the first layer has been exhausted or degraded, a second underlying layer having a second drug can release this drug for the next 30 to 40 days, and so on if so desired. In the example of FIG. 3B, for a stent (or other implantable device) manufactured from substrate 10, layer 64 can contain the first drug for release while layer 62 can contain the second drug for release after exhaustion or degradation of layer 64. The underlying layer 60 can omit any pharmaceutical agents to provide uncompromised structural support to the entire structure.

In other examples, rather than having each successive layer elute its respective drug, each layer 62, 64 (optionally layer 60 as well), can elute its respective drug simultaneously or at differing rates via a combination of diffusion and degradation. Although three layers are illustrated in this example, any number of layers can be utilized with any practicable combination of drugs for delivery. Moreover, the release kinetics of each drug from each layer can be altered in a variety of ways by changing the formulation of the drug-containing layer.

Examples of drugs or agents which can be loaded within certain layers of substrate 10 can include one or more anti-proliferative, anti-neoplastic, anti-genic, anti-inflammatory, and/or anti-restenotic agents. The therapeutic agents can also include anti-lipid, antimitotics, metalloproteinase inhibitors, anti-sclerosing agents. Therapeutic agents can also include peptides, enzymes, radio isotopes or agents for a variety of treatment options. This list of drugs or agents is presented to be illustrative and is not intended to be limiting.

Similarly, certain other layers can be loaded with radio-opaque substances such as platinum, gold, etc. to enable visibility of the stent under imaging modalities such as fluoroscopic imaging. Radio-opaque substances like tungsten, platinum, gold, etc. can be mixed with the polymeric solution and dip-coated upon the substrate such that the radio-opaque substances form a thin sub-micron thick layer upon the substrate. The radio-opaque substances can thus become embedded within layers that degrade in the final stages of degradation or within the structural layers to facilitate stent visibility under an imaging modality, such as fluoroscopy, throughout the life of the implanted device before fully degrading or losing its mechanical strength. Radio-opaque marker layers can also be dip-coated at one or both ends of substrate 10, e.g., up to 0.5 mm from each respective end. Additionally, the radio-opaque substances can also be spray-coated or cast along a portion of the substrate 10 between its proximal and distal ends in a radial direction by rotating mandrel 40 when any form of radio-opaque substance is to be formed along any section of length of substrate 10. Rings of polymers having radio-opaque markers can also be formed as part of the structure of the substrate 10.

Polymeric stents and other implantable devices made from such substrates can accordingly retain the material properties from the dip-coated polymer materials. The resulting stents, for instance, can exhibit mechanical properties which have a relatively high percentage ductility in radial, torsional, and/or axial directions. An example of this is a resulting stent having an ability to undergo a diameter reduction of anywhere between 5% to 70% when placed under an external load without any resulting plastic deformation. Such a stent can also exhibit high radial strength with, e.g., a 20% radial deformation when placed under a 0.1 N to 20 N load. Such a stent can also be configured to self-expand when exposed to normal body temperatures.

The stent can also exhibit other characteristic mechanical properties which are consistent with a substrate formed as described herein, for instance, high ductility and high strength polymeric substrates. Such substrates (and processed stents) can exhibit additional characteristics such as a percent reduction in diameter of between 5% to 70% without fracture formation when placed under a compressive load as well as a percent reduction in axial length of between 10% to 30% without fracture formation when placed under an axial load. Because of the relatively high ductility, the substrate or stent can also be adapted to curve up to 180° about a 1 cm curvature radius without fracture formation or failure. Additionally, when deployed within a vessel, a stent can also be expanded, e.g., by an inflatable intravascular balloon, by up to 5% to 70% to regain diameter without fracture formation or failure.

These values are intended to illustrate examples of how a polymeric tubing substrate and a resulting stent can be configured to yield a device with certain mechanical properties. Moreover, depending upon the desired results, certain tubes and stents can be tailored for specific requirements of various anatomical locations within a patient body by altering the polymer and/or copolymer blends to adjust various properties such as strength, ductility, degradation rates, etc.

Dip-coating can be used to impart an orientation between layers (e.g., linear orientation by dipping; radial orientation by spinning the mandrel, etc.) to further enhance the mechanical properties of the formed substrate. As radial strength is a desirable attribute of stent design, post-processing of the formed substrate can be accomplished to impart such attributes. Typically, polymeric stents suffer from having relatively thick walls to compensate for the lack of radial strength, and this, in turn, reduces flexibility, impedes navigation, and reduces arterial luminal area immediately post-implantation. Post-processing can also help to prevent material creep and recoil (creep is a time-dependent permanent deformation that occurs to a specimen under stress, typically under elevated temperatures) which are problems typically associated with polymeric stents.

In further increasing the radial or circumferential strength of the polymeric substrate, a number of additional processes can be applied to the substrate after the dip-coating procedure is completed (or close to being completed). A polymer that is amorphous or that is partially amorphous will generally undergo a transition from a pliable, elastic state (at higher temperatures) to a brittle glass-like state (at lower temperature) as it transitions through a particular temperature, referred as the glass transition temperature ($T_g$). The glass transition temperature for a given polymer will vary, depending on the size and flexibility of side chains, as well as the flexibility of the backbone linkages and the size of functional groups incorporated into the polymer backbone. Below $T_g$, the polymer will maintain some flexibility and can be deformed to a new shape. However, the further the temperature below $T_g$ the polymer is when being deformed, the greater the force needed to shape it.

Moreover, when a polymer is in glass transition temperature its molecular structure can be manipulated to form an orientation in a desired direction. Induced alignment of polymeric chains or orientation improves mechanical properties and behavior of the material. Molecular orientation is typically imparted by application of force while the polymer is in a pliable, elastic state. After sufficient orientation is induced, the temperature of the polymer is reduced to prevent reversal and dissipation of the orientation.

In one example, the polymeric substrate can be heated to increase its temperature along its entire length or along a selected portion of the substrate to a temperature that is at or above the $T_g$ of the polymer. For instance, for a substrate fabricated from PLLA, the substrate can be heated to a temperature between 60° C. to 70° C. Once the substrate has reached a sufficient temperature such that enough of its molecules have been mobilized, a force can be applied from within the substrate or along a portion of the substrate to increase its diameter from a first diameter $D_1$ to a second increased diameter $D_2$ for a period of time necessary to set the increased diameter. During this setting period, the application of force induces a molecular orientation in a circumferential direction to align the molecular orientation of polymer chains to enhance its mechanical properties. The re-formed substrate can then be cooled to a lower temperature typically below $T_g$, for example, by passing the tube through a cold environment, typically dry air or an inert gas to maintain the shape at diameter $D_2$ and prevent dissipation of molecular orientation.

The force applied to the substrate can be generated by a number of different methods. One method is by utilizing an expandable pressure vessel placed within the substrate. Another method is by utilizing a braided structure, such as a braid made from a super-elastic or shape memory alloy like NiTi alloy, to increase in size and to apply the desirable degree of force against the interior surface of the substrate.

Yet another method can apply the expansion force by application of a pressurized inert gas such as nitrogen within the substrate lumen.

Figure 4A:
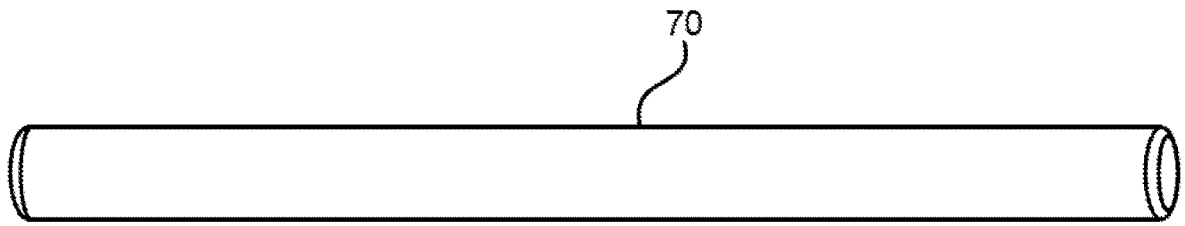
FIG. 4A illustrates an example of a polymeric base substrate which can be utilized to form any variation of the polymeric stents or scaffolds disclosed herein.

A polymeric substrate can also be formed, e.g., also via dip-coating, upon a mandrel to form a base polymeric substrate 70, as shown in FIG. 4A. The base polymeric substrate 70 can refer to another instance of the base polymeric substrate 10. In other variations, the base polymeric substrate 70 can be formed of an elastomeric bioabsorbable polymer, such as, but not limited to, poly-ε-caprolactone (PCL) or trimethylene carbonate (TMC), which can be dissolved in a compatible solvent such as dichloromethane (DCM).

The polymeric solution can be poured into a container and placed under the dip-coating assembly 30 in an inert environment. A mandrel that is attached to the dip-coating assembly 30 can be immersed into the solution to create the base layer of the composite stent structure. Once formed, the resulting polymeric substrate 70 can have an initial diameter, e.g., ranging generally from 2 mm to 10 mm, defined by the mandrel which is similar to the diameter of the ring structures 12. The substrate 70 can be formed to have an initial length ranging from 5 mm to 500 mm. The substrate 70 can be left upon the mandrel or removed and placed upon another mandrel.

Figure 4B:
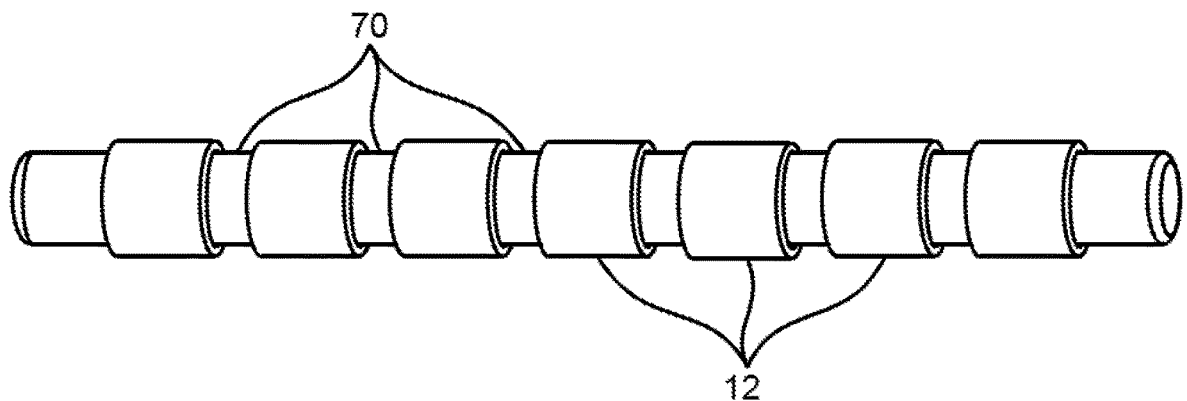
FIG. 4B illustrates an example of how the circular ring-like structures can be positioned or fitted upon a polymeric base substrate to form an intermediate layer of a composite stent structure.

In one variation, the ring structures 12 can be positioned upon the base polymeric substrate 70, as illustrated in FIG. 4B, at uniform intervals or at predetermined non-uniform distances from one another. The spacing between the ring structures 12 can be determined in part by the degree of flexibility desired of the resulting composite stent structure where the closer adjacent ring structures 12 are positioned relative to one another, the lesser resulting overall stent flexibility. Additionally, ring structures 12 can be positioned relatively closer to one another along a first portion of the composite stent and relatively farther from one another along a second portion of the stent. In one example, the ring structures 12 can be positioned at a uniform distance of 1 mm to 10 mm from one another.

If the ring structures 12 are formed to have a diameter which is slightly larger than a diameter of the base polymeric substrate 70, the ring structures 12 can be compressed to reduce their diameters such that the ring structures 12 are overlaid directly upon the outer surface of the substrate 70. In use, the ring structures 12 can be compressed to a second smaller diameter for delivery through the vasculature of a patient to a region to be treated. When deployed, the ring structures 12 (as well as the base substrate 70 and overlaid substrate 71) can be expanded back to their initial diameter or to a diameter less than the initial diameter.

Figure 4C:
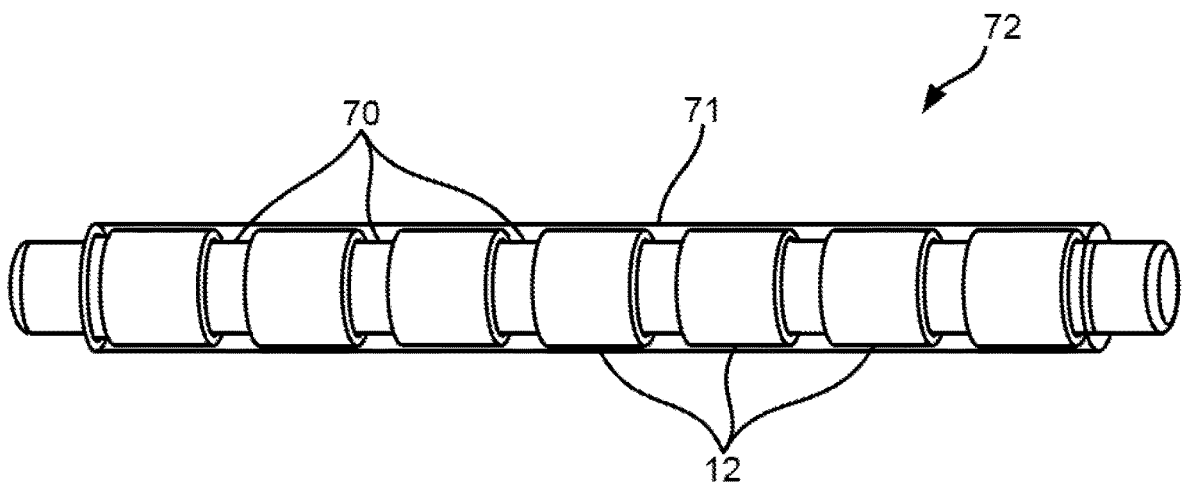
FIG. 4C illustrates an example composite structure formed with an additional polymeric layer overlaid atop the polymeric base substrate and ring structures.

The ring and substrate structure can then be immersed again in the same or different polymeric solution as base polymeric substrate 70 to form an additional polymeric substrate 71 overlaid upon the base substrate 70 and ring structures 12 to form the composite stent structure 72, as illustrated in FIG. 4C. The ring structures 12 can be encapsulated or otherwise encased entirely between the base substrate 70 and the overlaid substrate 71 such that the ring structures 12 are connected or otherwise attached to one another entirely via the elastomeric sections.

Additionally, either or both of the ring structures 12 and base or overlaid substrate layers 70, 71 can be configured to retain and deliver or elute any number of pharmaceutical agents, such as an anti-proliferative, an anti-restenotic, etc.

Because the elastomeric polymer substrate couples the ring structures 12 to one another rather than an integrated structural connecting member between the ring structures themselves, the ring structures 12 can be adjustable along an axial or radially direction independent of one another allowing for any number of configurations and adjustments of the stent structure 72 for conforming within and bending with a vessel which other coated stent structures are unable to achieve.

Figure 5:
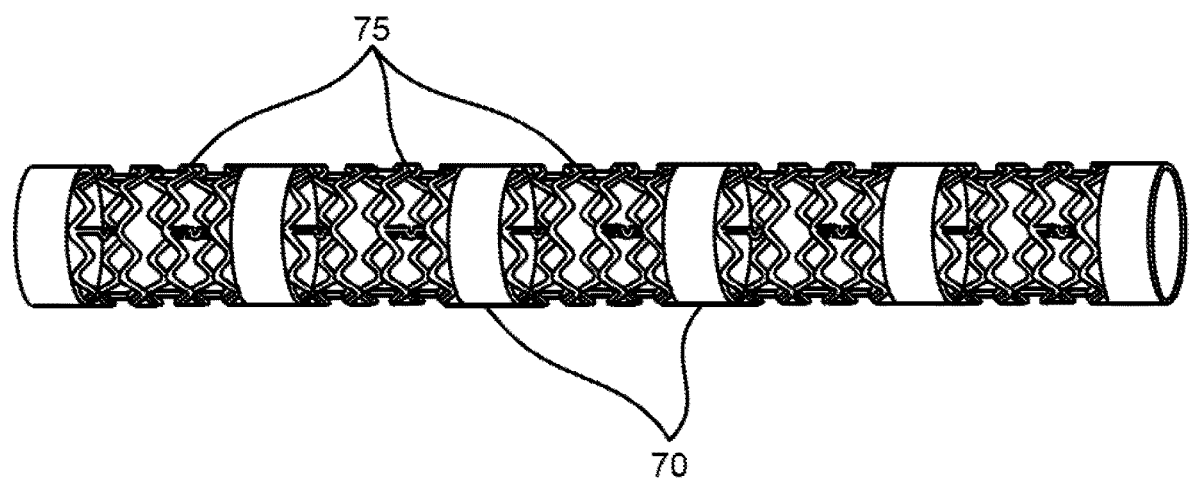
FIG. 5 illustrates an example composite structure where the ring structures can be patterned to form a scaffold structure.

This resulting stent structure 72 can be removed from the mandrel and machined to length, if necessary, and additional post-processing can be performed upon the stent as well. For instance, the stent structure 72 can have one or more of the ring structures 12 machined into patterned polymeric rings 75 such as expandable scaffold structures, e.g., by laser machining, as illustrated in FIG. 5. In machining the stent structure, the process of removing material from the polymeric rings 75 can at least partially expose portions of the polymeric rings 75 to the environment. For example, the inner surfaces and the outer surfaces of the polymeric rings 75 can remain coated or covered by both respective base and overlaid substrate layers 70, 71 while side surfaces of the rings 75 can become exposed by removal of the substrate layers as well as portions of the ring material as the stent structure is machined. These exposed surfaces can be re-coated, if desired, or left exposed to the environment.

Figure 6:
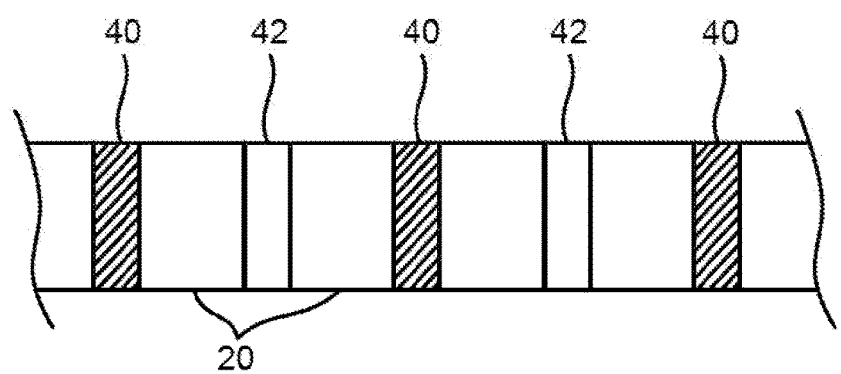
FIG. 6 illustrates an example composite structure where ring structures can be alternated between rings fabricated from different polymeric substrates.

The polymeric ring structures 12 utilized in the composite stent structure 72 can be fabricated from a common substrate and common polymers. However, in other variations, the ring structures forming the stent 24 can be fabricated from different substrates having different material characteristics. FIG. 6 illustrates an example where a first set of polymeric rings 76 can be positioned in an alternating pattern with a second set of polymeric rings 77 along the base substrate 70. In this and other examples, the overlaid polymeric substrate 71 can be omitted from the figures merely for clarity.

Figure 7:
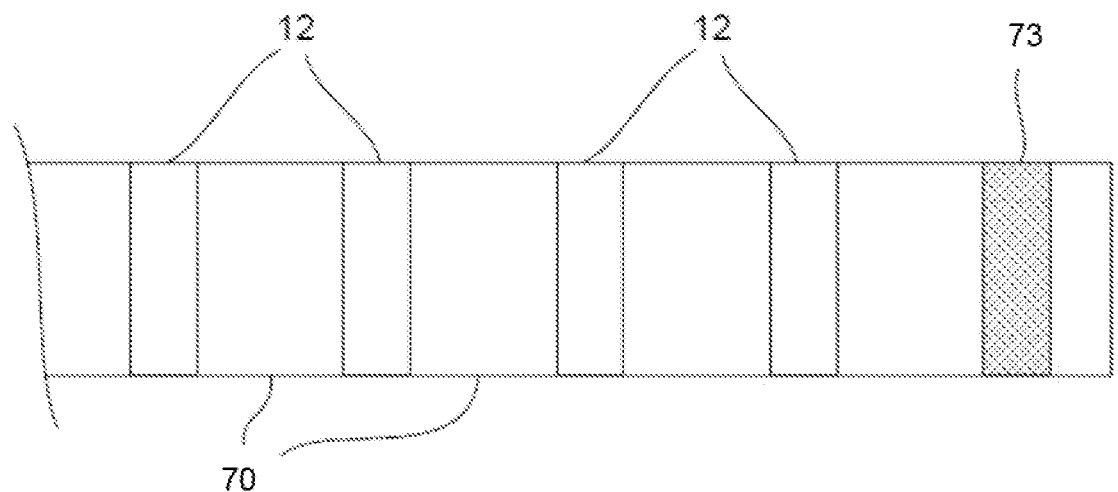
FIG. 7 illustrates an example composite structure where one or more flexible terminal rings can be formed for overlapping between adjacently deployed stents.

Another variation is illustrated in FIG. 7, which shows an example where a first set of polymeric ring structures 12 can be positioned along the stent with a flexible polymeric ring 73 fabricated to be relatively more flexible than the remaining ring structures 12 positioned along a terminal end of the stent structure.

Figure 8:
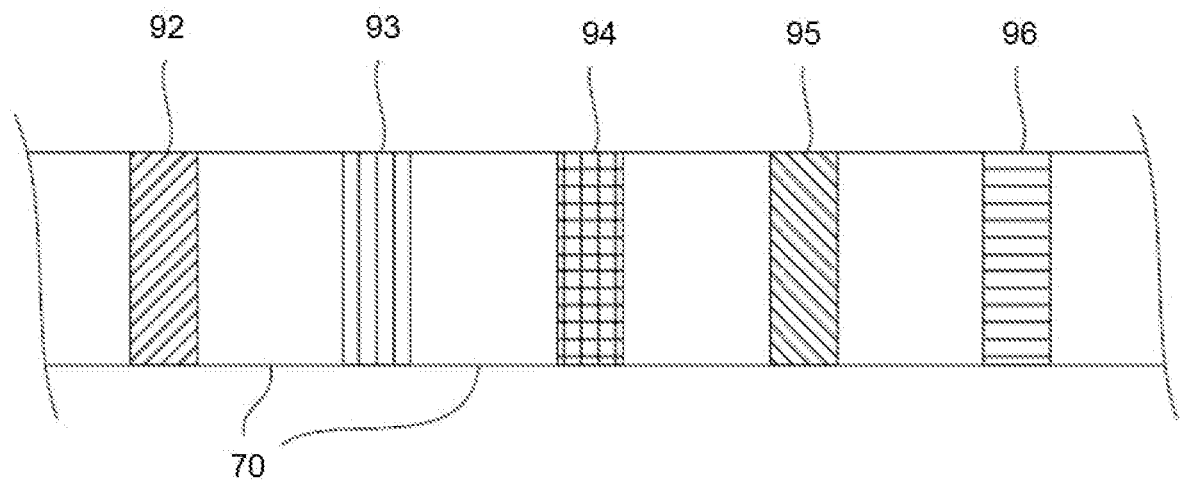
FIG. 8 illustrates an example composite structure where each ring structure along the composite stent can be fabricated from polymeric substrates different from one another.

Yet another example is illustrated in FIG. 8 where each of the ring structures can be fabricated from different substrates and polymers. For example, a stent structure can be fabricated to have a first polymeric ring 92, a second polymeric ring 93, a third polymeric ring 94, a fourth polymeric ring 95, a fifth polymeric ring 96, and so on to form a composite stent structure. An example of use can include a composite stent structure for placement within a tapered or diametrically expanding vessel where each subsequent ring structure can be fabricated to be more radially expandable than an adjacent ring structure, e.g., where the first polymeric ring 92 can be radially expandable to a first diameter, second polymeric ring 93 is radially expandable to a second diameter larger than the first diameter, third polymeric ring 94 can be radially expandable to a third diameter larger than the second diameter, and so on. This is intended to be exemplary and other examples are, of course, intended to be within the scope of this disclosure.

Figure 9:
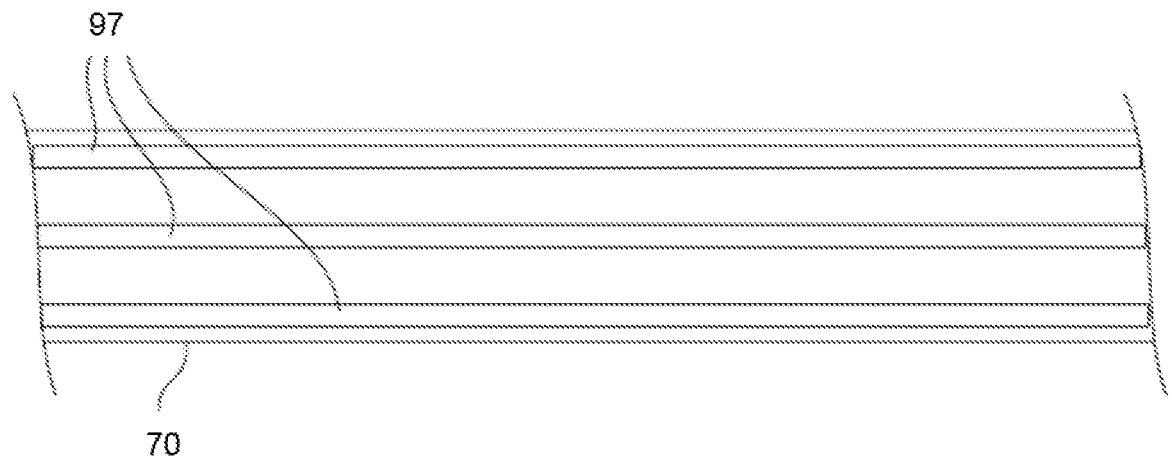
FIG. 9 illustrates an example composite structure where the intermediate polymeric layer is formed as longitudinal strips rather than ring structures.
Figure 10:
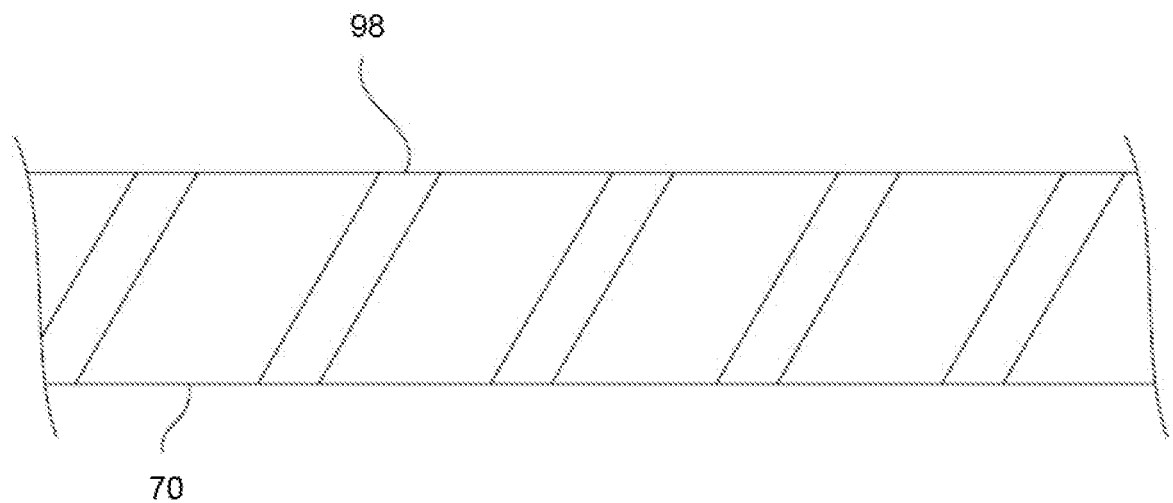
FIG. 10 illustrates an example composite structure where the intermediate polymeric layer is formed as a helical structure between the base layer and overlaid layer.

Yet another variation is shown in FIG. 9, which illustrates longitudinally-oriented polymeric strips 97 rather than ring structures positioned along the base substrate 70. In this example, such a composite stent structure can be configured to allow for greater flexibility under radial stresses. Another example is illustrated in FIG. 10 which shows a helically-oriented polymeric member 98 which can be positioned along base substrate 70.

As described in U.S. patent application Ser. No. 12/143,659 incorporated hereinabove, the polymeric substrate utilized to form the ring structures can be heat treated at, near, or above the glass transition temperature $T_g$ of the substrate to set an initial diameter and the substrate can then be processed to produce the ring structures having a corresponding initial diameter. The resulting composite stent structure can be reduced from its initial diameter to a second delivery diameter which is less than the initial diameter such that the composite stent structure can be positioned upon, e.g., an inflation balloon of a delivery catheter. The composite stent structure at its reduced diameter can be self-constrained such that the stent remains in its reduced diameter without the need for an outer sheath, although a sheath can be optionally utilized. Additionally, the composite stent structure can be reduced from its initial diameter to its delivery diameter without cracking or material failure.

Figure 11A:
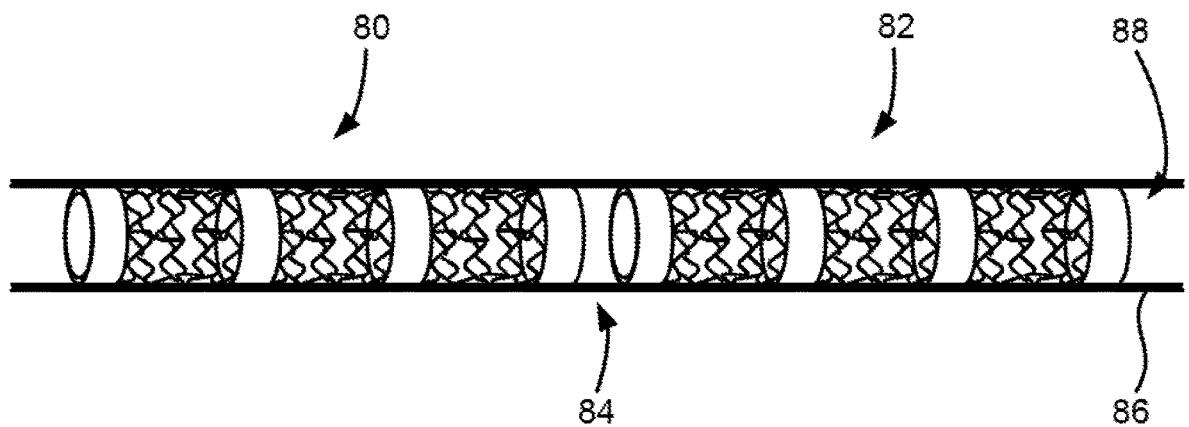
FIG. 11A illustrates an example of adjacent composite structures deployed within a vessel with a gap or spacing between the two structures.

With the composite stent structure positioned upon a delivery catheter, the stent can be advanced intravascularly within the lumen 88 of a vessel 86 until the delivery site is reached. The inflation balloon can be inflated to expand a diameter of composite stent structure into contact against the vessel interior, e.g., to an intermediate diameter, which is less than the stent's initial diameter yet larger than the delivery diameter. The composite stent structure can be expanded to this intermediate diameter without any cracking or failure because of the inherent material characteristics, as shown in FIG. 11A. Moreover, expansion to the intermediate diameter can allow for the composite stent structure to securely contact the vessel wall while allowing for the withdrawal of the delivery catheter.

Once the composite stent structure has been expanded to some intermediate diameter and secured against the vessel wall 86, the composite stent structure can be allowed to then self-expand further over a period of time into further contact with the vessel wall such that composite stent structure conforms securely to the tissue. This self-expansion feature ultimately allows for the composite stent structure to expand back to its initial diameter which had been heat-set in the ring structures or until the composite stent structure has fully self-expanded within the confines of the vessel lumen 88. In yet another variation, the composite stent structure can be expanded directly to its final diameter, e.g., by balloon inflation, without having to reach an intermediate diameter and subsequent self-expansion.

Figure 11B:
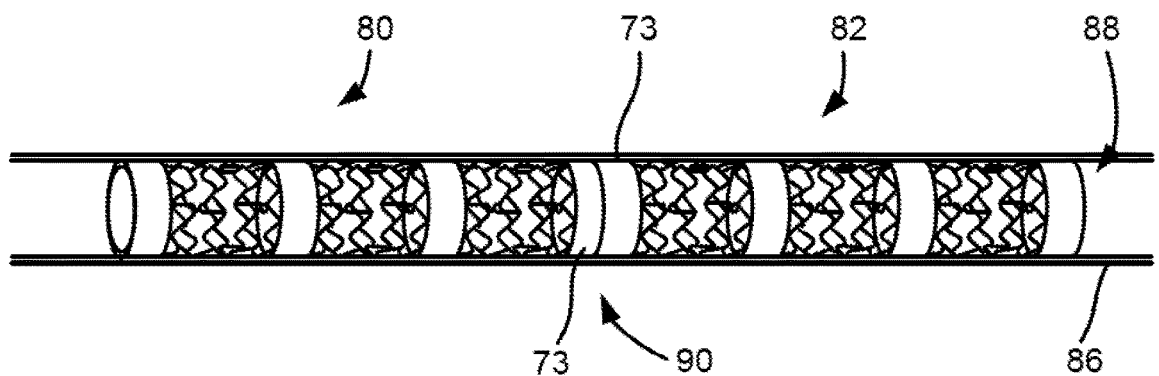
FIG. 11B illustrates another example of adjacent composite structures deployed within a vessel with the terminal ends of the structures overlapping with one another.

In the example illustrated, a first composite stent 80 is shown deployed within vessel lumen 88 adjacent to a second composite stent 82 with spacing 84 between the stents. Additional stent structures can be deployed as well depending upon the length of the lesion to be stented. FIG. 11B illustrates another example where adjacent composite stents 80, 82 are deployed within vessel lumen 88 with their terminal ends overlapping one another along overlapped portion 90. As the SFA tends to develop long, diffuse lesions with calcification, multiple stents can be deployed with overlapping ends. However, as this overlapping can cause regions or locations of increased stress that can initiate fracturing along the stent and lead to potential stent failure and closure of the vessel, the terminal ring structures of both overlapped composite stents 80, 82 can be fabricated from an elastomeric polymer allowing for the overlap to occur along these segments. Such overlapping would not significantly compromise axial flexibility and the composite stents can continue its compliance with the arterial movement.

Figure 12:
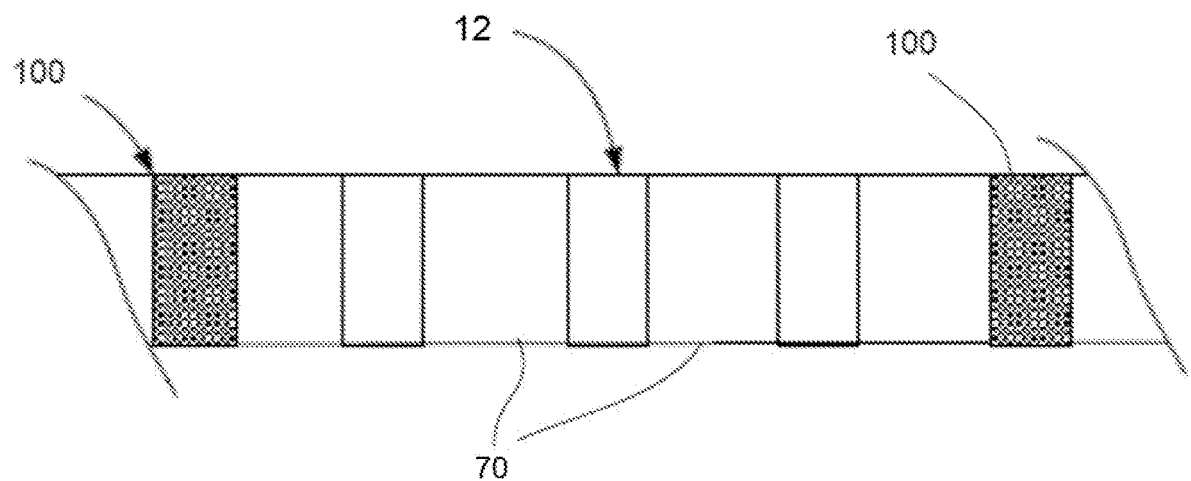
FIG. 12 illustrates a side view of an example composite structure where the terminal ring structures are configured to degrade at a relatively faster rate than the remaining ring structures.

Another variation which facilitates the overlapping of adjacent stents is shown in the side view of FIG. 12. The overlaid substrate has been omitted for clarity only and can be included as a layer positioned atop the base substrate 70 as well as the polymeric rings, as previously described. As illustrated, the polymeric ring structures 12 can include terminal polymeric rings 100 which are fabricated to degrade at a relatively faster rate than the remaining ring structures 12 positioned between these terminal rings 100. Such a composite stent structure can allow for the optimal overlapping of multiple stents along the length of a blood vessel.

Figure 13A:
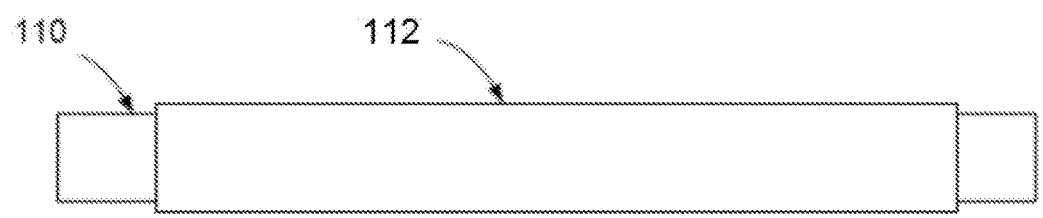
FIGS. 13A and 13B illustrate side views of an example composite structure where polymeric ring structures are positioned along a flexible base coat in a separate manufacturing operation.
Figure 13B:
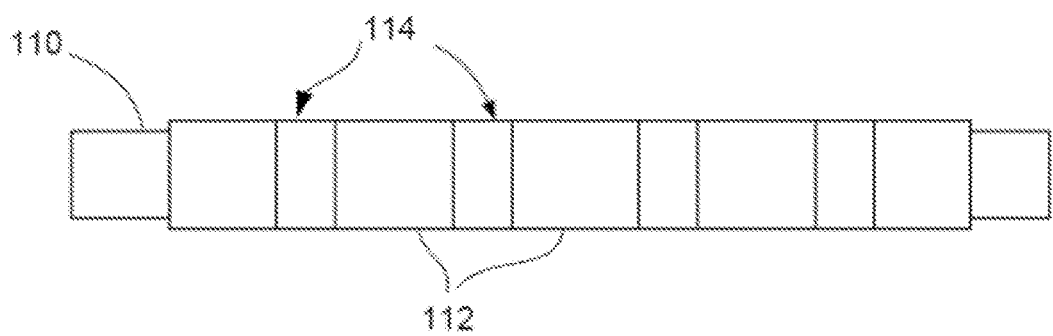

Yet another variation is shown in the side views of FIGS. 13A and 13B which illustrate a mandrel 110 that is provided with a flexible polymeric base substrate 112 placed or formed thereon. A set of polymeric ring structures 114 can be positioned along the longitudinal axis of the flexible base coat 112 in a separate manufacturing operation.

Figure 14A:
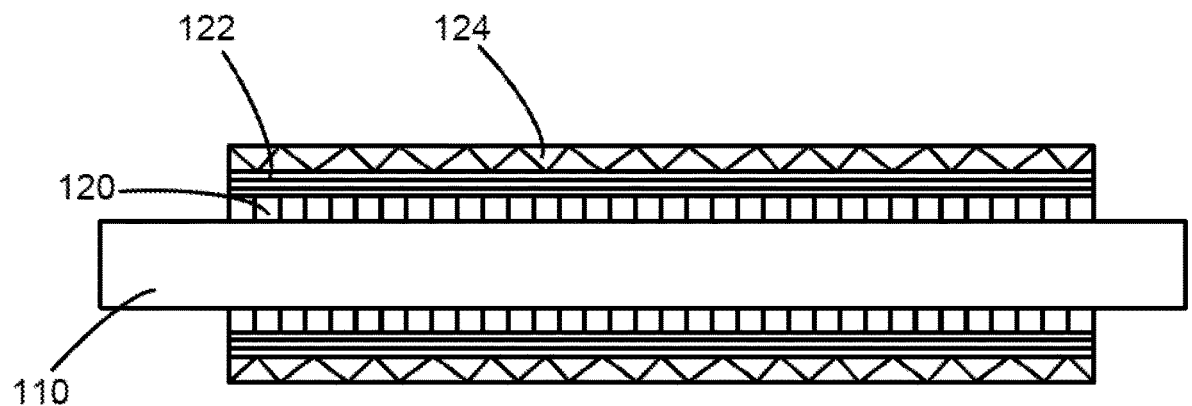
FIGS. 14A and 14B illustrate partial cross-sectional side and end views, respectively, of a composite structure formed by sandwiching a high-strength polymeric material between two or more layers of a flexible polymer to provide for greater flexibility under radial stress while retaining relatively high strength.
Figure 14B:
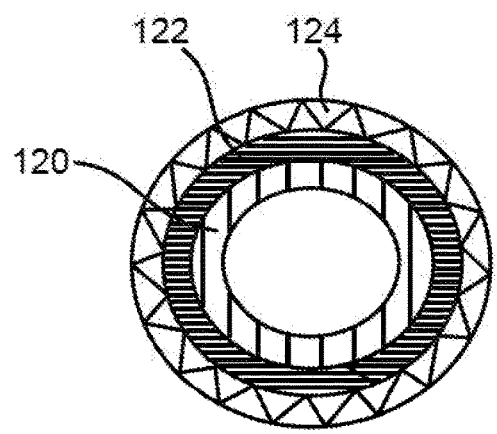

Another variation is illustrated in the partial cross-sectional side and end views, respectively, of FIGS. 14A and 14B. In this example, a composite structure can be provided by forming a composite stent structure having multiple polymeric layers. For instance, a middle layer 122 can be made of a high strength polymeric material such as poly-L-lactic acid (PLLA) or poly-L-lactide that is sandwiched between two or more layers 120, 124 of a flexible polymer such as poly-t-caprolactone (PCL). Such a composite stent structure can be configured to allow for greater flexibility under radial stresses while retaining relatively high strength provided by the middle layer 122 comprising PLLA.

Figure 15A:
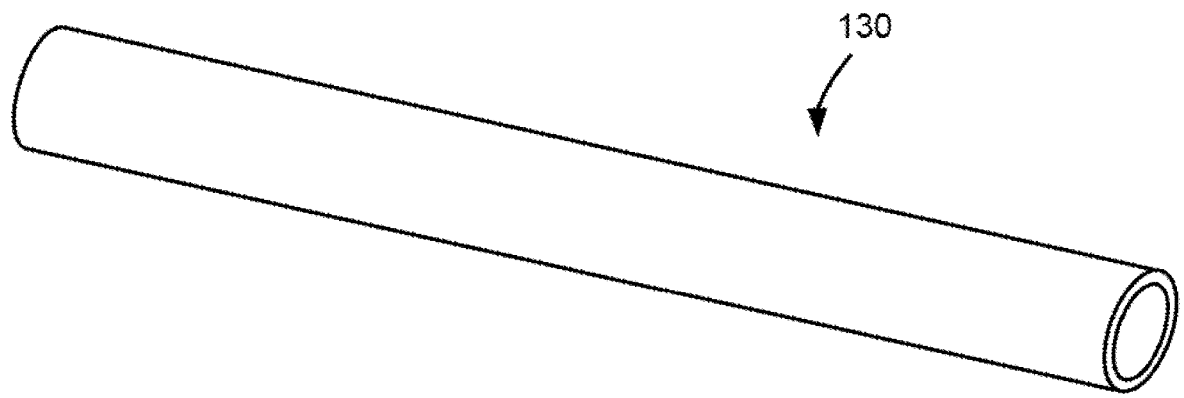
FIG. 15A illustrates a perspective view of an example polymeric substrate.
Figure 15B:
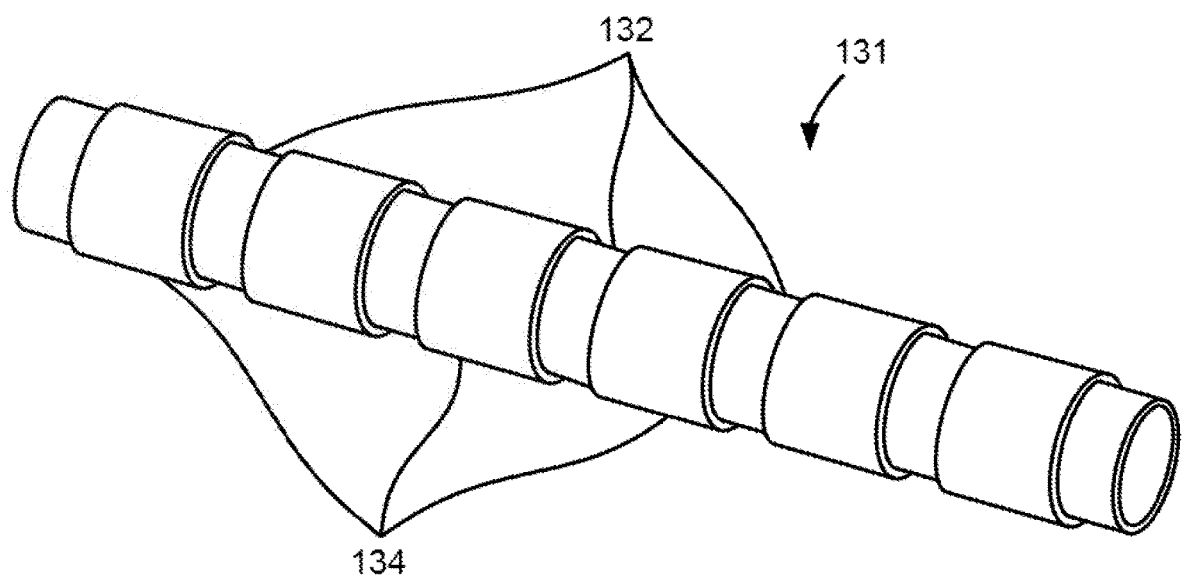
FIG. 15B illustrates the polymeric substrate of FIG. 15A machined into segments having reduced diameters.

In yet other alternative variations for forming composite structures, a bioabsorbable polymeric substrate 130 initially formed by the dip-coating process as previously described can be formed into a tubular substrate as shown in the perspective view of FIG. 15A. Substrate 130 can be further processed, such as by machining, to form a machined substrate 131, as shown in the perspective view of FIG. 15B, having one or more reduced segments 132 which are reduced in diameter alternating with the relatively thicker segments 134 which can be reduced in diameter to a lesser degree or uncut altogether. The number of reduced segments 132 and the spacing between can be uniform or varied depending upon the desired resulting stent or scaffold and the reduction in diameter of these segments 132 can also be varied as well. In one example, for a given initial diameter of 2 to 12 mm of substrate 130, segments 132 can be reduced in diameter by, e.g., 1.85 mm to 11.85 mm. Moreover, although the example shown in FIG. 15B shows seven reduced segments 132 between thicker segments 134, this number can be varied depending upon the desired resulting lengths of segments 132, e.g., ranging from 0.5 mm to 3 mm in length.

In forming the substrate to have a variable wall thickness as illustrated, laser machining (profiling) of the outer diameter can be utilized. The integrity and material properties of the substrate material are desirably maintained during this process of selectively removing material in order to achieve the desired profile. An ultra-short pulse femtosecond type laser can be used to selectively remove the material from the reduced segments 132 by taking advantage, e.g., of multi-photon absorption, such that the laser removes the material without modifying the material integrity. Thus, the mechanical properties and molecular structure of the bioabsorbable substrate 130 can be unaffected during this machining process.

Some of the variables in utilizing such a laser for this particular application can include, e.g., laser power level, laser pulse frequency, energy profile of the beam, beam diameter, lens focal length, focal position relative to the substrate surface, speed of the substrate/beam relative to the substrate, and any gas jet/shield either coaxial or tangential to the material, etc. By adjusting some or all of these variables, a multi-level profile can be readily produced. In one example, increasing or decreasing the rotational speed of the substrate relative to the laser during processing will vary the depth of penetration. This in combination with a translation rate of the substrate relative to the laser can also be varied to produce a relatively sharp edge in the relief area or a smooth tapered transition between each of the adjacent segments. Varying both parameters along the longitudinal axis of the substrate 130 can produce a continuously variable profile from which a stent pattern can be cut, as further described below.

The laser system can comprise an ultra-short pulse width laser operating in the femtosecond pulse region, e.g., 100 to 500 fs typical pulse width, and a wavelength, $\lambda$, e.g., in the near to mid-IR range (750 to 1600 nm typical $\lambda$). The pulse frequency of these lasers can range from single pulse to kilohertz (1 to 10 kHz typical). The beam energy profile can be $TEM_{00}$ to a high order mode ($TEM_{00}$ is typical, but not necessary). The beam delivery system can comprise a beam bender, vertical mounted monocular viewing/laser beam focusing head, focusing lens and coaxial gas jet assembly. A laser system can also include a linear stage having a horizontally mounted rotary stage with a collet clamping system mounted below the focusing/cutting head.

With the substrate tube 130 clamped by the rotary stage and held in a horizontal plane, the laser beam focusing head can be positioned perpendicular to the longitudinal axis of substrate 130. Moving the focus of the beam away from the outer diameter of the tubing, a non-penetrating channel can be machined in the substrate 130. Controlling the speed of rotation and/or linear translation of the tube under the beam, a channel can be machined along the substrate axis. Varying any one or all of the parameters (e.g., position, depth, taper, length, etc.) of machining can be controlled and positioned along the entire length of the substrate 130. The ability to profile the substrate 130 can provide a number of advantages in the flexibility of the resulting stent design and performance. For example, such profiling can improve the flexibility of the stent geometry and expansion capability in high stress areas, expose single or multiple layers to enhance or expose drug delivery by placing non-penetrating holes into one or more particular drug-infused layer(s) of the substrate 130 or by placing grooves or channels into these drug layer(s). Moreover, the ability to profile the substrate 130 can allow for a substrate having a variable profile which can be over-coated with the same or different polymer, as described herein.

Figure 15C:
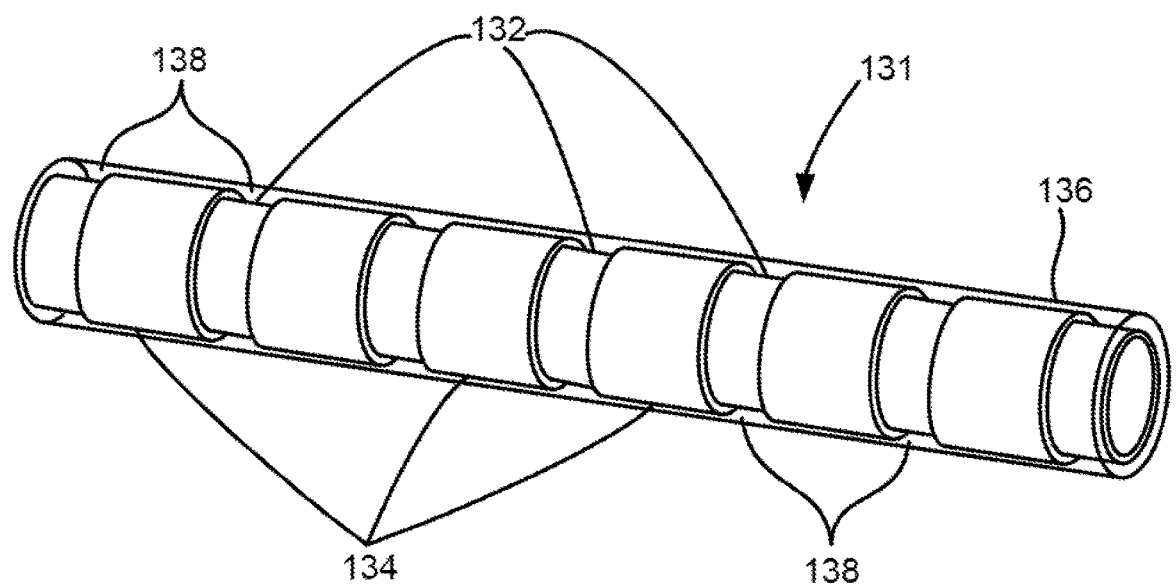
FIG. 15C illustrates a perspective view of an example of the machined substrate further coated by one or more polymeric layers.
Figure 15D:
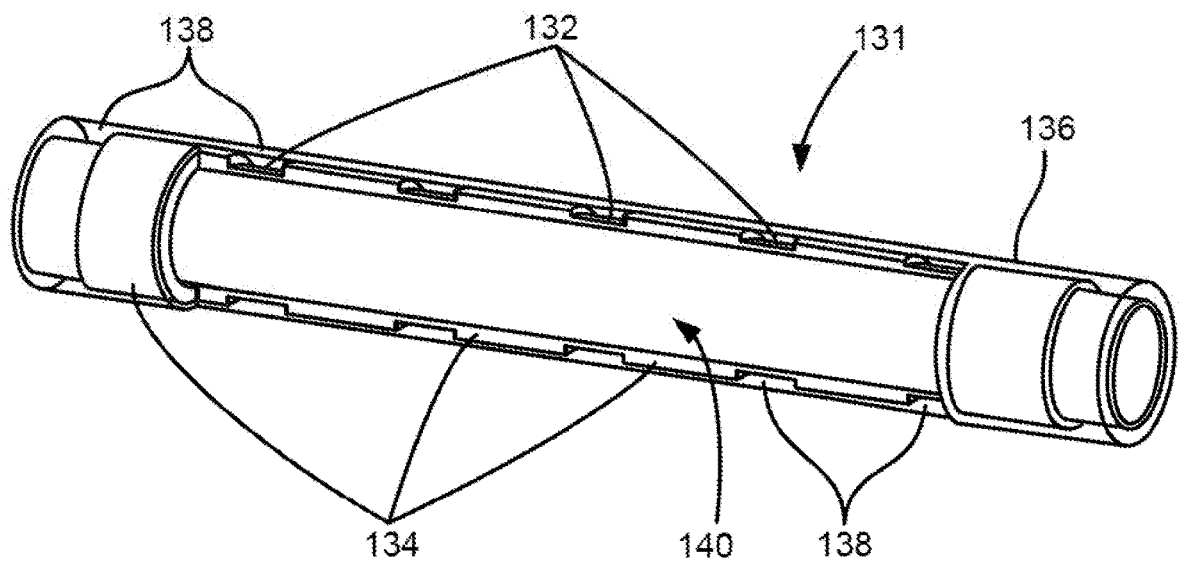
FIG. 15D illustrates a perspective partial cutaway view of an example of the machined substrate further coated by one or more polymeric layers.

Once machined substrate 131 has been sufficiently processed, it can then be coated, e.g., via the dip-coating process as previously described, such that one or more additional elastomeric polymer layers are coated upon substrate 131. The example shown in the perspective view of FIG. 15C illustrates machined substrate 131 having at least one additional elastomeric polymer layer 136 coated thereupon; however, other variations can have more than one layer coated atop one another depending upon the desired characteristics of the resulting substrate. Additionally, each subsequent layer coated upon machined substrate 131 can be of the same, similar, or different material from polymeric substrate 131, e.g., polyethylene, polycarbonates, polyamides, polyesteramides, polyetheretherketone, polyacetals, poly ketals, polyurethane, polyolefin, polyethylene terephthalate, polylactide, poly-L-lactide, poly-glycolide, poly (lactide-co-glycolide), polycaprolactone, caprolactones, polydioxanones, polyanhydrides, polyorthocarbonates, polyphosphazene, chitin, chitosan, poly(amino acids), polyorthoesters, oligomers, homopolymers, methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide, ethacrylamide, styrene, vinyl chloride, vinyl pyrrolidone, polyvinyl alcohol, polycaprolactam, polylauryl lactam, polyhexamethylene adipamide, polyhexamethylene dodecanediamide, trimethylene carbonate, poly($\beta$-hydroxybutyrate), poly(g-ethyl glutamate), poly(DTH iminocarbonate), poly(bisphenol A iminocarbonate), polycyanoacrylate, polyphosphazene, methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide, ethacrylamide, and copolymers, terpolymers and combinations and mixtures thereof, etc., again depending upon the desired resulting characteristics. The one or more polymeric layers 136 can be coated upon machined substrate 131 such that the elastomeric polymer 136 forms within the reduced segments 132 as well as upon segments 134. The resulting coated layer 136 can range in thickness accordingly from, e.g., 50 µm to 500 µm, such that the layer 136 forms a uniform outer diameter along the length of substrate 131. As shown in the perspective partial cutaway view of FIG. 15D, the thickened elastomeric polymer segments 138 formed along reduced segments 132 can be seen along substrate 131 with substrate lumen 140 defined therethrough.

With machined substrate 131 coated with the one or more polymeric layers 136, the entire formed substrate can then be processed, e.g., machined, laser-machined, etc., to form a stent or scaffold (for example, the stent or scaffold 150 shown in FIG. 16, 17, 19, or 20).

Figure 16:
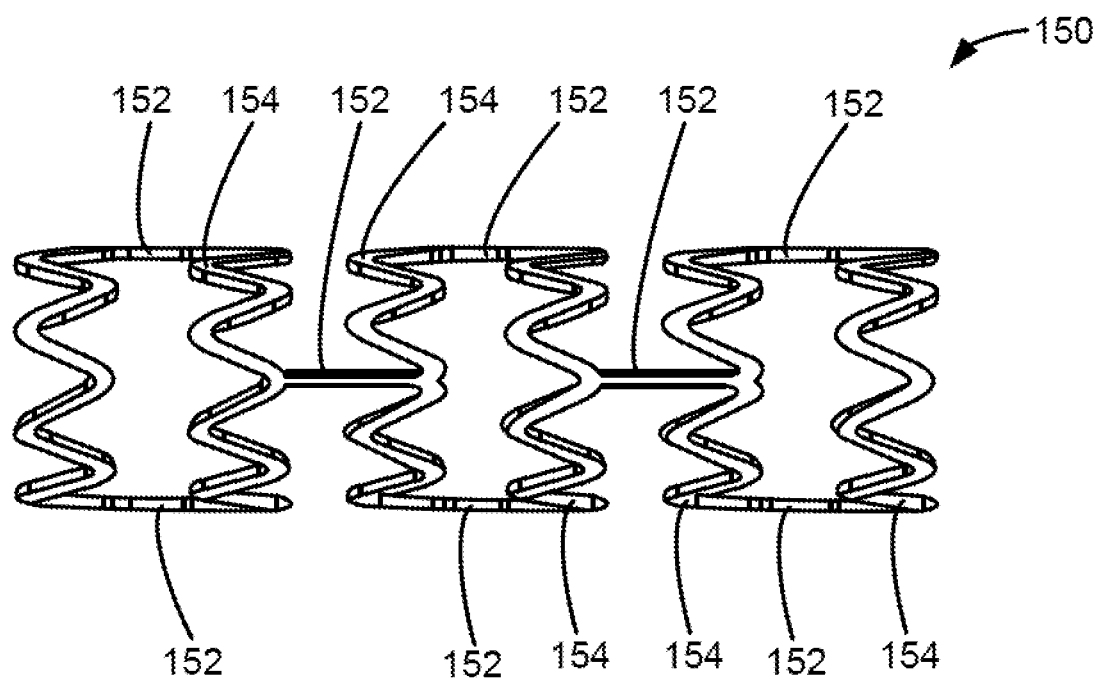
FIG. 16 illustrates a portion of an example of a stent or scaffold which can be formed from any of the polymeric substrates disclosed herein having ring structures connected by struts.

FIG. 16 is a side view of a portion of an example composite stent or scaffold 150 which can be formed (e.g., machined, laser cut, etc.) from a base polymeric substrate such as, for example, base polymeric substrate 10 or base polymeric substrate 70.

Examples of polymers which can be utilized to form the base polymeric substrate or layer can include, but is not limited to, polyethylene, polycarbonates, polyamides, polyesteramides, polyetheretherketone, polyacetals, polyketals, polyurethane, polyolefin, or polyethylene terephthalate and biodegradable or bioabsorbable polymers, for example, polylactide (PLA) including poly-L-lactide (PLLA), polyglycolide (PGA), poly(lactide-co-glycolide) (PLGA) or polycaprolactone or poly-caprolactone (PCL), caprolactones, polydioxanones, polyanhydrides, polyorthocarbonates, polyphosphazenes, chitin, chitosan, poly(amino acids), and polyorthoesters, and copolymers, terpolymers and combinations, blends, or mixtures thereof.

Other examples of suitable polymers can include synthetic polymers, for example, oligomers, homopolymers, and co-polymers, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyls acetate; polymers formed of ethylene, propylene, and tetrafluoroethylene. Further examples can include nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketones.

Examples of other biodegradable polymers which can be used to form part of the composite stent or scaffold include, but is not limited to, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and copolymers, terpolymers and combinations and mixtures thereof. There are also a number of biodegradable polymers derived from natural sources such as modified polysaccharides (cellulose, chitin, chitosan, dextran) or modified proteins (fibrin, casein).

Other examples of suitable polymers can include synthetic polymers, for example, oligomers, homopolymers, and co-polymers, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyls acetate; polymers formed of ethylene, propylene, and tetrafluoroethylene. Further examples can include nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polyacetals, polyketals, polydimethylsiloxanes, and polyetherketones.

The example composite stent or scaffold 150 can comprise polymeric ring structures 154 and one or more interconnecting struts 152 which extend between and couple adjacent ring structures 154. When the polymeric ring structures 154 are made from a base polymeric layer which has been formed via a dip-coating process (such as any of the dip-coating processes described with respect to FIG. 2A, 2B, 2C, 3A, 3B, or 3C) or other finishing processes, the polymeric ring structures 154 can retain a molecular weight and mechanical strength of the starting substrate or the base polymeric substrate. When the base polymeric substrate is made from a bioabsorbable or biodegradable polymeric substance, such as any of PLA, PLLA, PGA, PLGA, PCL, caprolactones, polydioxanones, polyanhydrides, polyorthocarbonates, polyphosphazenes, chitin, chitosan, poly (amino acids), and polyorthoesters, copolymers thereof terpolymers thereof, or combinations and mixtures thereof, the polymeric ring structures 154 can be bioabsorbable or biodegradable.

The polymeric ring structures 154 can be formed at a first diameter and be radially compressible to a smaller second diameter or a deployment diameter. The polymeric ring structures 154 can be re-expandable or self-expandable to the larger first diameter when deployed within the vasculature of a patient. As illustrated in FIG. 16, the polymeric ring structures 154 can be axially or longitudinally separated from one another and adjacent polymeric ring structures 154 can be connected or coupled by one or more interconnecting struts 152. Each of the interconnecting struts 152 can have a width which is less than a circumference of one of the polymeric ring structures 154. The polymeric ring structures 154 can be axially and rotationally movable relative to one another via the interconnecting struts 152. The one or more interconnecting struts 152 can also be made of bioabsorbable polymers, polymer blends, or co-polymer such that the entire composite stent structure 150 can be bioabsorbable.

The interconnecting struts 152 can be formed from a polymer blend, a blend of polymer solutions, or co-polymer comprising poly-L-lactide (PLLA) and an elastomeric polymer. In certain variations, the polymer blend or co-polymer can have a glass transition temperature between 50° C. and 65° C.

In one variation, the elastomeric polymer can be or comprise polycaprolactone (PCL). The PCL can be about 1% to about 10% (for example, weight/weight or volume/volume) of the polymer blend or co-polymer. In other variations, the PCL can be about 1% to about 50% (for example, weight/weight or volume/volume) of the polymer blend or co-polymer. When the interconnecting struts 152 are made of one or more elastomeric polymers, at least one of the interconnecting struts 152 can be more elastic than the polymeric ring structures 154.

In one variation, the polymeric ring structures 154 can be spaced closer to one another along a first portion than along a second portion of the composite stent structure 150. In this and other variations, a terminal ring structure (for example, a terminal ring structure positioned similar to the terminal ring 73 of FIG. 7) can be relatively more flexible than a remainder of the polymeric ring structures 154.

As shown in the example composite stent or scaffold 150 of FIG. 16, the plurality of interconnecting struts 152 can be positioned along a length of the composite stent or scaffold 150 in a circumferentially alternating manner between immediately adjacent ring structures 154. In other variations not shown in the figures, the interconnecting struts 152 can be longitudinally aligned with one another along a length of the composite stent or scaffold 150.

In another variation, the composite stent or scaffold 150 can be formed from a coated substrate 131 such that the interconnecting struts 152 are formed from thickened elastomeric polymer segments 138 while the polymeric ring structures 154 are formed on the polymeric substrate 131. This can result in a contiguous and uniform composite stent or scaffold 150 which comprises high-strength circumferential segments or ring structures 154 connected to one another via elastomeric interconnecting struts 152 such that the composite stent or scaffold 150 exhibits high-strength characteristics yet is flexible overall.

Figure 17:
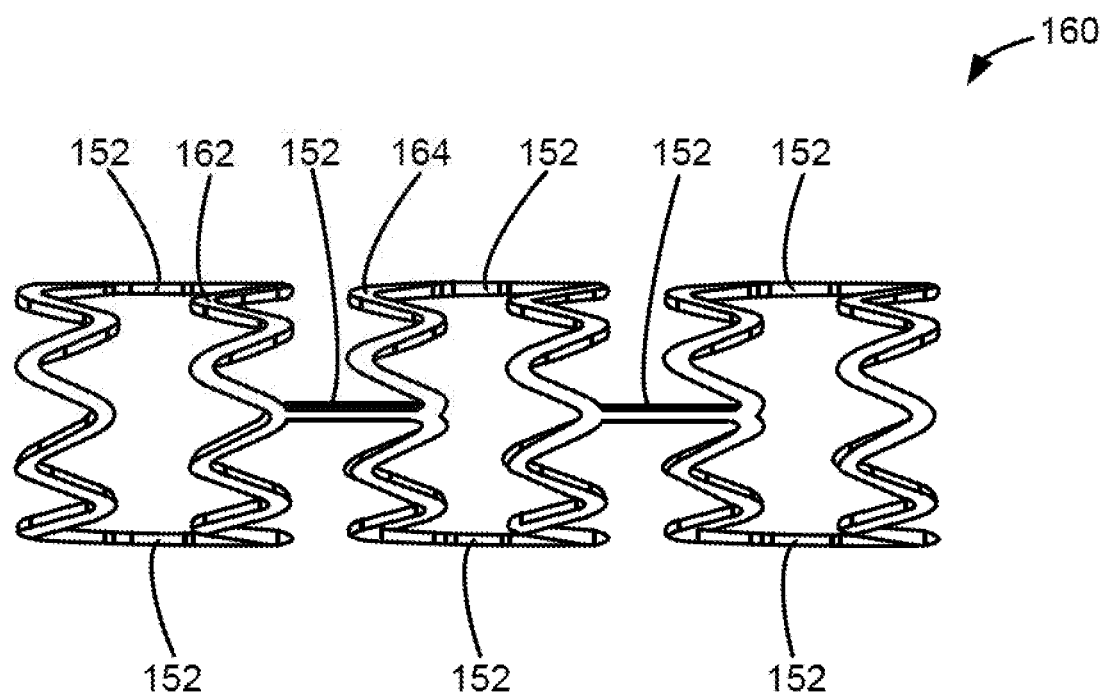
FIG. 17 illustrates a portion of another example of a stent or scaffold which can be formed from any of the polymeric substrates disclosed herein having ring structures connected by struts.

FIG. 17 is a side view of a portion of a variation of a composite stent or scaffold 160 comprising a first polymeric ring structure 162 and a second polymeric ring structure 164 connected by one or more interconnecting struts 152. In this variation, the first polymeric ring structure 162 can be made from a base polymeric substrate comprising an elastomeric bioabsorbable polymer resin such as PCL or TMC while the adjacent second polymeric ring structure 164 can be made from only the base polymeric substrate or another polymeric substrate comprising a different polymer blend or composition.

In yet another variation, the composite stent or scaffold 160 structure can be formed from the coated polymeric substrate 131 such that the first polymeric ring structure 162 is formed from the elastomeric polymer segments 138 while an adjacent second polymeric ring structure 164 is formed from polymeric substrate 131 such that the second polymeric ring structure 164 is relatively higher in strength than the first polymeric ring structure 162, which is relatively more flexible. The alternating segments of elastomeric segments and substrate segments can be repeated along a portion or the entire length of the composite stent or scaffold 160 depending upon the desired degree of flexibility and strength characteristics. Moreover, other variations of alternating between the segments can be employed.

Figure 18A:
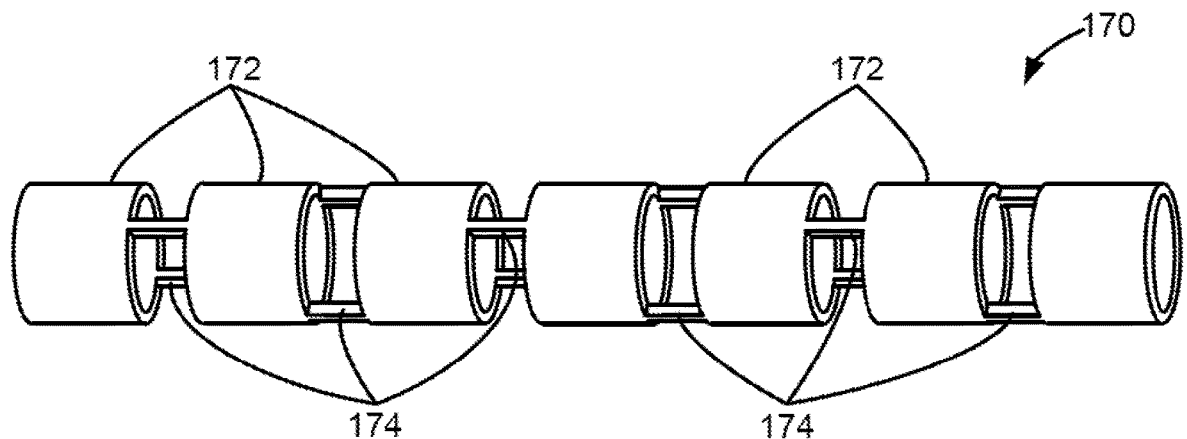
FIGS. 18A and 18B illustrate an example polymeric substrate which has been machined to form ring segments connected via connecting members.
Figure 18B:
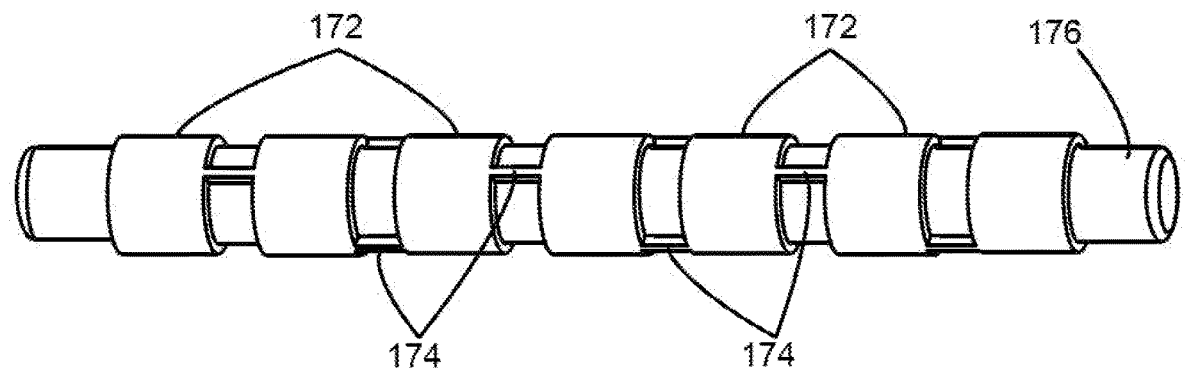

FIG. 18A illustrates an example of polymeric substrate 170 which has been machined to form ring segments 172 connected via one or more interconnecting struts 174. The polymeric substrate 170 can be initially formed from a dip-coated base polymeric substrate such as base polymeric substrate 10 or base polymeric substrate 70. The dip-coated base polymeric substrate can be machined or laser cut into a number of ring segments 172 connected via interconnecting struts 174. Although seven ring segments 172 are shown in this example, fewer than or greater than seven ring segments 172 can be utilized. In one variation, the interconnecting struts 174 can be fashioned into alternating apposed members between adjacent ring segments 172. For example, the interconnecting struts 174 can be positioned along a length of the polymeric substrate 170 in a circumferentially alternating manner between immediately adjacent ring segments 172. Once the polymeric substrate 170 has been desirably machined or cut, the polymeric substrate 170 can be positioned upon mandrel 176, as shown in FIG. 18B.

Figure 18C:
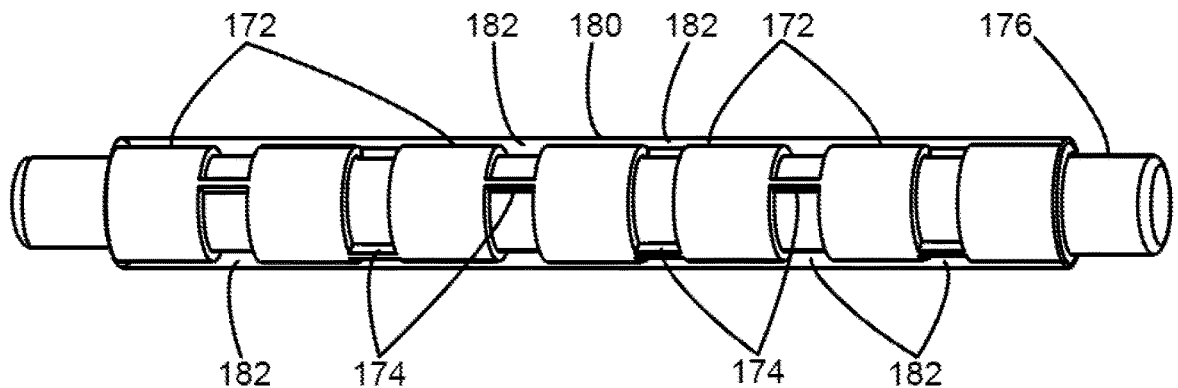
FIGS. 18C and 18D illustrate an example of the machined substrate coated by one or more polymeric layers and a partial cutaway view of the machined substrate coated by the one or more polymeric layers, respectively.
Figure 18D:
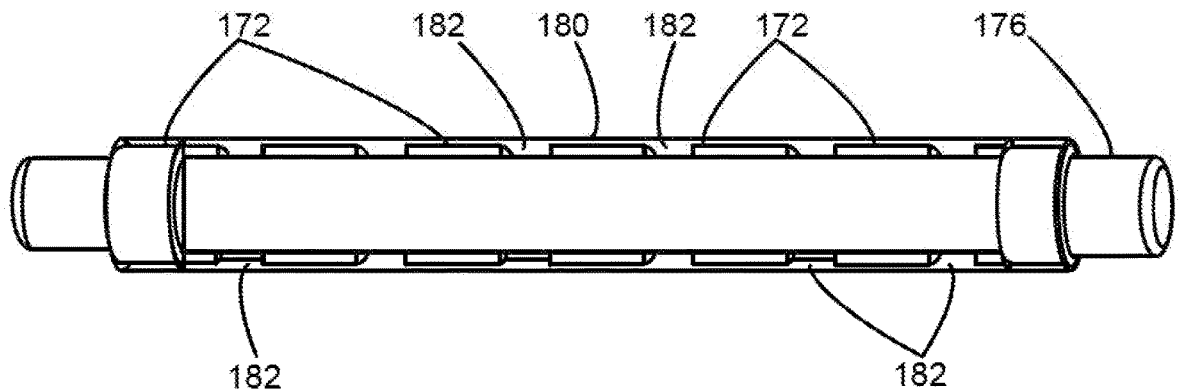

In one variation, the mandrel 176 and the entire machined polymeric substrate 170 can then be coated again, e.g., via dip-coating as previously described, by one or more layers of bioabsorbable elastomeric polymers 180 (e.g., PCL). The one or more layers of bioabsorbable elastomeric polymers 180 can form thickened elastomeric interconnecting strut sections 182 as well as thickened elastomeric ring segments 172, as shown in FIGS. 18C and 18D. In other variations not shown in FIG. 18C but contemplated by this disclosure, the one or more layers of bioabsorbable elastomeric polymers 180 (e.g., PCL) can cover only the interconnecting struts 174. All such composite machined or cut substrates can then be further processed, machined or cut to form one or more composite stent or scaffolds having various unique or advantageous composite structural characteristics.

Figure 19:
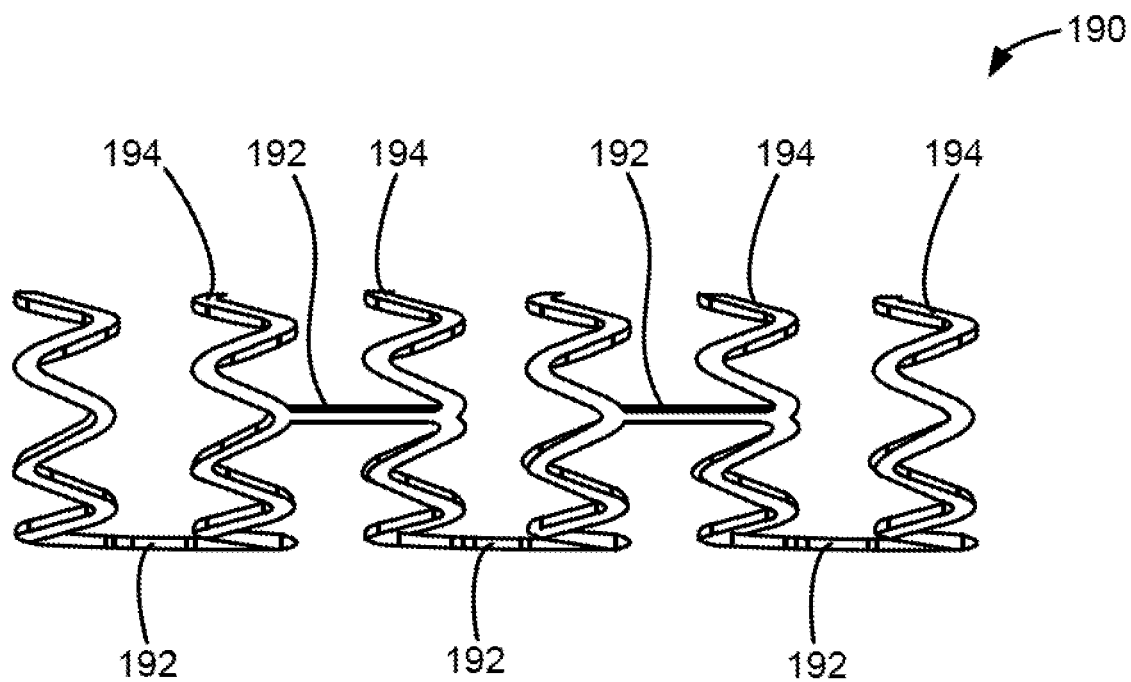
FIG. 19 illustrates a portion of another example of a stent or scaffold which can be formed from any of the polymeric substrates disclosed herein having ring structures connected by struts.

FIG. 19 is a side view of a portion of an example composite stent or scaffold 190. The composite stent or scaffold 190 can comprise polymeric ring structures 194 and one or more interconnecting struts 192 which extend between and coupled adjacent polymeric ring structures 194.

In certain variations, the polymeric ring structures 194 can be made from a dip-coated base polymeric substrate such as base polymeric substrate 10 or base polymeric substrate 70.

Examples of polymers which can be utilized to form the base polymeric substrate or layer can include, but is not limited to, polyethylene, polycarbonates, polyamides, polyesteramides, polyetheretherketone, polyacetals, polyketals, polyurethane, polyolefin, or polyethylene terephthalate and biodegradable or bioabsorbable polymers, for example, polylactide (PLA) including poly-L-lactide (PLLA), polyglycolide (PGA), poly(lactide-co-glycolide) (PLGA) or polycaprolactone or poly-ε-caprolactone (PCL), caprolactones, polydioxanones, polyanhydrides, polyorthocarbonates, polyphosphazenes, chitin, chitosan, poly(amino acids), and polyorthoesters, and copolymers, terpolymers and combinations, blends, or mixtures thereof.

Other examples of suitable polymers can include synthetic polymers, for example, oligomers, homopolymers, and co-polymers, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyls acetate; polymers formed of ethylene, propylene, and tetrafluoroethylene. Further examples can include nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polylactic acid, polyglycolic acid, polydimethylsiloxanes, and polyetherketones.

Examples of other biodegradable polymers which can be used to form part of the composite stent or scaffold include, but is not limited to, trimethylene carbonate, poly(β-hydroxybutyrate), poly(g-ethyl glutamate), poly(DTH iminocarbonate), poly(bisphenol A iminocarbonate), poly(ortho ester), polycyanoacrylate, and copolymers, terpolymers and combinations and mixtures thereof. There are also a number of biodegradable polymers derived from natural sources such as modified polysaccharides (cellulose, chitin, chitosan, dextran) or modified proteins (fibrin, casein).

Other examples of suitable polymers can include synthetic polymers, for example, oligomers, homopolymers, and co-polymers, acrylics such as those polymerized from methyl acrylate, methyl methacrylate, acrylic acid, methacrylic acid, acrylamide, hydroxyethyl acrylate, hydroxyethyl methacrylate, glyceryl acrylate, glyceryl methacrylate, methacrylamide and ethacrylamide; vinyls such as styrene, vinyl chloride, vinyl pyrrolidone, polyvinyl alcohol, and vinyls acetate; polymers formed of ethylene, propylene, and tetrafluoroethylene. Further examples can include nylons such as polycaprolactam, polylauryl lactam, polyhexamethylene adipamide, and polyhexamethylene dodecanediamide, and also polyurethanes, polycarbonates, polyamides, polysulfones, poly(ethylene terephthalate), polyacetals, polyketals, polydimethylsiloxanes, and polyetherketones.

When the polymeric ring structures 194 are made from a base polymeric layer which has been formed via a dip-coating process (such as any of the dip-coating processes described with respect to FIG. 2A, 2B, 2C, 3A, 3B, or 3C) or other finishing processes, the polymeric ring structures 194 can retain a molecular weight and mechanical strength of the starting substrate or the base polymeric substrate. In addition, when the base polymeric substrate is made from a bioabsorbable or biodegradable polymeric substance, such as any of PLA, PLLA, PGA, PLGA, PCL, caprolactones, polydioxanones, polyanhydrides, polyorthocarbonates, polyphosphazenes, chitin, chitosan, poly(amino acids), and polyorthoesters, copolymers thereof, terpolymers thereof, or combinations and mixtures thereof, the polymeric ring structures 194 can be bioabsorbable or biodegradable.

The polymeric ring structures 194 can be formed at a first diameter and be radially compressible to a smaller second diameter or a deployment diameter. The polymeric ring structures 194 can be re-expandable or self-expandable to the larger first diameter when deployed within the vasculature of a patient. As illustrated in FIG. 19, the polymeric ring structures 194 can be axially or longitudinally separated from one another and adjacent polymeric ring structures 194 can be connected or coupled by the one or more interconnecting struts 192. Each of the interconnecting struts 192 can have a width which is less than a circumference of one of the polymeric ring structures 194. The polymeric ring structures 194 can be axially and rotationally movable relative to one another via the interconnecting struts 192. The one or more interconnecting struts 192 can also be made of bioabsorbable polymers, polymer blends, or co-polymer such that the entire composite stent structure 190 is bioabsorbable.

The interconnecting struts 192 can be formed from a polymer blend, a blend of polymer solutions, or co-polymer comprising poly-L-lactide (PLLA) and an elastomeric polymer. In certain variations, the polymer blend or co-polymer can have a glass transition temperature between 50° C. and 65° C.

In one variation, the elastomeric polymer can be or comprise polycaprolactone (PCL). The PCL can be about 1% to about 10% (for example, weight/weight or volume/volume) of the polymer blend or co-polymer. In other variations, the PCL can be about 1% to about 50% (for example, weight/weight or volume/volume) of the polymer blend or co-polymer. When the interconnecting struts 192 are made of one or more elastomeric polymers, at least one of the interconnecting struts 192 can be more elastic than the polymeric ring structures 194.

In one variation, the polymeric ring structures 194 can be spaced closer to one another along a first portion than along a second portion of the composite stent structure 190. In this and other variations, a terminal ring structure (for example, a terminal ring structure positioned similar to the terminal ring 73 of FIG. 7) can be relatively more flexible than a remainder of the polymeric ring structures 194.

As shown in the example composite stent or scaffold 190 of FIG. 19, the plurality of interconnecting struts 192 can be positioned along a length of the composite stent or scaffold 190 in a circumferentially alternating manner between immediately adjacent ring structures 194. In other variations not shown in the figures, the interconnecting struts 192 can be longitudinally aligned with one another along a length of the composite stent or scaffold 190.

In another variation, the interconnecting struts 192 can be formed from the thickened elastomeric interconnecting strut sections 182 while the polymeric ring structures 194 can be formed from the ring segments 172.

The resulting composite stent or scaffold 190 allows for the structure to have significant flexibility along the axial, torsional, and/or bending directions as well as the ability to withstand relatively long fatigue cycles without formation of cracks or fractures, e.g., 1,000,000 to 3,000,000 cycles, in axial compression, extension, and torsional modes. Also, the stent or scaffold 190 can also withstand a pulsatile fatigue life of up to, e.g., 120,000,000 cycles or more.

Figure 20:
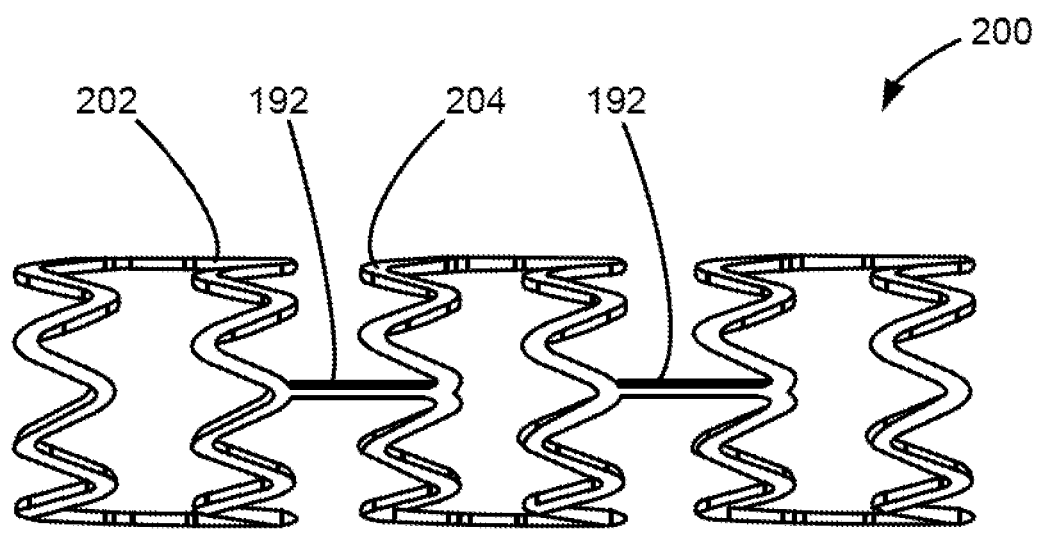
FIG. 20 illustrates a portion of another example of a stent or scaffold which can be formed from any of the polymeric substrates disclosed herein having ring structures connected by struts.

FIG. 20 is a side view of a portion of a variation of a composite stent or scaffold 200 comprising a first polymeric ring structure 202 and a second polymeric ring structure 204 connected by one or more interconnecting struts 192. In this variation, the first polymeric ring structure 202 can be made from a base polymeric substrate comprising an elastomeric bioabsorbable polymer resin such as PCL, TMC, or DCM while the adjacent second polymeric ring structure 204 can be made from only the base polymeric substrate or another polymeric substrate comprising a different polymer blend or composition. In this and other variations, the interconnecting struts 192 can also alternate such that one interconnecting strut 192 can be elastomeric while another adjacent or neighboring interconnecting strut 192 can be non-elastomeric or be made from a polymeric blend or solution having a different percentage of elastomeric polymers.

The applications of the disclosed invention discussed above are not limited to certain processes, treatments, or placement in certain regions of the body, but can include any number of other processes, treatments, and areas of the body. Modification of the above-described methods and devices for carrying out the invention and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A bioabsorbable composite stent structure, comprising:
    bioabsorbable polymeric ring structures which retain a molecular weight and mechanical strength of a starting substrate, the ring structures having a formed first diameter and being radially compressible to a smaller second diameter and re-expandable to the first diameter, wherein the ring structures are separated from one another and comprise a base polymeric layer;
    one or more interconnecting struts which extend between and couple adjacent ring structures, wherein the interconnecting struts each has a width which is less than a circumference of one of the ring structures,
        wherein the interconnecting struts are formed from a polymer blend or co-polymer of poly-L-lactide (PLLA) and an elastomeric polymer,
        wherein the adjacent ring structures are axially and rotationally movable relative to one another via the interconnecting struts, and
        wherein the one or more interconnecting struts are bioabsorbable.

2. The stent structure of claim 1, wherein the elastomeric polymer is polycaprolactone (PCL).

3. The stent structure of claim 2, wherein the PCL is 1% to 10% of the polymer blend or co-polymer.

4. The stent structure of claim 2, wherein the PCL is 1% to 50% of the polymer blend or co-polymer.

5. The stent structure of claim 1, wherein the polymer blend or co-polymer has a glass transition temperature between 50° C. and 65° C.

6. The stent structure of claim 1, wherein the ring structures are spaced closer to one another along a first portion than along a second portion of the stent structure.

7. The stent structure of claim 1, wherein a terminal ring structure is relatively more flexible than a remainder of the ring structures.

8. The stent structure of claim 1, wherein the base polymeric layer is a bioabsorbable polymeric substrate formed via a dip-coating process.

9. A bioabsorbable composite stent structure, comprising:
bioabsorbable polymeric ring structures which retain a molecular weight and mechanical strength of a starting substrate, the ring structures having a formed first diameter and being radially compressible to a smaller second diameter and re-expandable to the first diameter, wherein the ring structures are separated from one another and comprise a base polymeric layer;
a plurality of interconnecting struts which extend between and couple adjacent ring structures, wherein the interconnecting struts each has a width which is less than a circumference of one of the ring structures,
wherein the interconnecting struts are formed from a polymer blend or co-polymer of poly-L-lactide (PLLA) and an elastomeric polymer,
wherein the plurality of interconnecting struts are positioned along a length of the stent structure in a circumferentially alternating manner between immediately adjacent ring structures,
wherein the ring structures are spaced closer to one another along a first portion than along a second portion of the stent structure, and
wherein the one or more interconnecting struts are bioabsorbable.

10. The stent structure of claim 9, wherein the elastomeric polymer is polycaprolactone (PCL).

11. The stent structure of claim 10, wherein the PCL is 1% to 10% of the polymer blend or co-polymer.

12. The stent structure of claim 10, wherein the PCL is 1% to 50% of the polymer blend or co-polymer.

13. The stent structure of claim 9, wherein the polymer blend or co-polymer has a glass transition temperature between 50° C. and 65° C.

14. The stent structure of claim 9, wherein the base polymeric layer is a bioabsorbable polymeric substrate formed via a dip-coating process.

15. A bioabsorbable composite stent structure, comprising:
bioabsorbable polymeric ring structures which retain a molecular weight and mechanical strength of a starting substrate, the ring structures having a formed first diameter and being radially compressible to a smaller second diameter and re-expandable to the first diameter, wherein the ring structures are separated from one another and comprise a base polymeric layer;
one or more interconnecting struts which extend between and couple adjacent ring structures, wherein the interconnecting struts each has a width which is less than a circumference of one of the ring structures,
wherein the interconnecting struts are formed from a polymer blend or co-polymer of poly-L-lactide (PLLA) and an elastomeric polymer,
wherein the one or more interconnecting struts is more elastic than the ring structures,
wherein a terminal ring structure is relatively more flexible than a remainder of the ring structures, and
wherein the one or more interconnecting struts are bioabsorbable.

16. The stent structure of claim 15, wherein the elastomeric polymer is polycaprolactone (PCL).

17. The stent structure of claim 16, wherein the PCL is 1% to 10% of the polymer blend or co-polymer.

18. The stent structure of claim 16, wherein the PCL is 1% to 50% of the polymer blend or co-polymer.

19. The stent structure of claim 15, wherein the polymer blend or co-polymer has a glass transition temperature between 50° C. and 65° C.

20. The stent structure of claim 15, wherein the base polymeric layer is a bioabsorbable polymeric substrate formed via a dip-coating process.

* * * * *